US008552064B2

(12) United States Patent
Doncel

(10) Patent No.: US 8,552,064 B2
(45) Date of Patent: *Oct. 8, 2013

(54) SURAMIN AND DERIVATIVES THEREOF AS TOPICAL MICROBICIDE AND CONTRACEPTIVE

(75) Inventor: Gustavo F. Doncel, Norfolk, VA (US)

(73) Assignee: Eastern Virginia Medical School, Norfolk, VA (US)

( * ) Notice: Subject to any disclaimer, the term of this patent is extended or adjusted under 35 U.S.C. 154(b) by 56 days.

This patent is subject to a terminal disclaimer.

(21) Appl. No.: 12/340,339

(22) Filed: Dec. 19, 2008

(65) Prior Publication Data
US 2009/0220574 A1    Sep. 3, 2009

Related U.S. Application Data

(62) Division of application No. 10/508,566, filed on Mar. 11, 2005, now Pat. No. 7,476,693.

(51) Int. Cl.
*A61K 31/185* (2006.01)
*C07C 39/00* (2006.01)

(52) U.S. Cl.
USPC .......................................... 514/577; 562/89

(58) Field of Classification Search
USPC ........................................... 514/577; 562/89
See application file for complete search history.

(56) References Cited

U.S. PATENT DOCUMENTS

| | | | |
|---|---|---|---|
| 4,816,254 A | 3/1989 | Moss | |
| 5,013,544 A | 5/1991 | Chantler et al. | |
| 5,158,940 A | 10/1992 | LaRocca et al. | |
| 5,173,509 A | 12/1992 | Walther et al. | |
| 5,192,788 A | 3/1993 | Dixon et al. | |
| 5,299,581 A | 4/1994 | Donnell et al. | |
| 5,407,919 A | 4/1995 | Brode et al. | |
| 5,482,053 A | 1/1996 | Kelly | |
| 5,589,510 A | 12/1996 | Ono et al. | |
| 5,624,675 A | 4/1997 | Kelly | |
| 5,853,742 A | 12/1998 | Bartolone et al. | |
| 5,877,213 A | 3/1999 | Samid | |
| 5,886,000 A | 3/1999 | Shoji et al. | |
| 5,932,619 A | 8/1999 | Zaneveld et al. | |
| 5,958,399 A | 9/1999 | Sonderfan et al. | |
| 5,985,275 A * | 11/1999 | Neurath et al. | 424/133.1 |
| 6,028,115 A | 2/2000 | Zaneveld et al. | |
| 6,121,320 A | 9/2000 | Doukas | |
| 6,140,368 A | 10/2000 | Kenyon et al. | |
| 6,239,182 B1 | 5/2001 | Zaneveld et al. | |
| 6,365,625 B1 | 4/2002 | Singh et al. | |
| 7,476,693 B2 | 1/2009 | Doncel | |
| 2002/0035061 A1 | 3/2002 | Krieger et al. | |
| 2002/0071863 A1 | 6/2002 | Dong et al. | |
| 2002/0077365 A1 | 6/2002 | Windsor et al. | |

FOREIGN PATENT DOCUMENTS

| | | |
|---|---|---|
| AU | 636255 | 4/1993 |
| EP | 0183352 A2 | 6/1986 |
| EP | 0355245 A1 | 2/1990 |
| EP | 0387314 B1 | 9/1990 |
| EP | 0402078 | 12/1990 |
| EP | 0486809 A2 | 5/1992 |
| EP | 514553 | 11/1992 |
| EP | 0564307 | 10/1993 |
| GB | 2217602 | 11/1989 |
| GB | 2260701 A | 4/1993 |
| WO | WO-91/07982 | 6/1991 |
| WO | WO-9107982 | 6/1991 |
| WO | WO-93/07864 A1 | 4/1993 |
| WO | WO-95/08981 | 4/1995 |
| WO | WO-9903463 | 1/1999 |
| WO | WO-02/20726 A2 | 3/2002 |
| WO | WO-02053096 | 7/2002 |
| WO | WO-03/082193 A2 | 10/2003 |

OTHER PUBLICATIONS

European Patent Application No. 03721455 Supplementary Search Report (search completed May 9, 2008) (3 pages).
PCT/US03/09127 International Search Report (mailed May 12, 2004) (4 pages).
Xingquan et al. "Drug inhibition of equine infectious anemia virus and human immunodeficiency virus," Chinese Journal of Virology, 8(1): (6 Pages) (Mar. 1992).
"Microbicide Pipeline Requires $600 Mil. Over 10 Years—Rockfeller's Chen" The Blue Sheet, Policy and Biomedical Research, vol. 44, No. 027, p. 7 (2001).
Anderson et al. "Evaluation of Poly (Styrene-4-Sulfonate) as a Preventive Agent for Conception and Sexually Transmitted Diseases." Journal of Andrology, Vo. 21, No. 6, p. 862-875 (2000).
Aronson et al. "Lysomal Hyaluronidase from Rat Liver." The Journal of Biological Chemistry, vol. 242, No. 3, p. 437-440 (1967).
Balzarini et al. "Comparative Inhibitory Effects of Suramin and Other Selected Compounds on the Infectivity and Replication of Human T-Cell Lyphotronic Virus (HTLV-III) Lymphadenopathy-Associated Virus (LAV)." Int. J. Cancer, vol. 7, p. 451-457 (1986).
Balzarini et al. "Preclinical Studies on Thiocarboxanilide UC-781 as a Virucidal Agent" AIDS, vol. 12, pp. 1129-1138 (1998).
Balzarini, et al. "Differential Antiherpesvirus and Antiretrovirus Effects of the (S) and (R) Enantiomers of Acyclic Nucleoside Phosphonates: Potent and Selective in Vitro and in Vivo Antiretrovirus Activities of (R)-9-(2-Phosphonomethoxypropyl)-2,6-Diaminopurine" Antimicorbial Agents and Chemotherapy, vol. 37, No. 2, pp. 332-338 (1993).
Barnhart et al. "Distribution of a Spermicide Containing Nonoxynol-9 in the Vaginal Canal and the Upper Female Reproductive Tract" Human Reproduction, vol. 16, No. 6, pp. 1151-1154 (2001).
Barnhart et al. "Distribution of Topical Medication in the Human Vagina as Imaged by Magnetic Resonance Imaging" Fertility and Sterility, Vo. 76, No. 1, pp. 189-195 (2001).
Blair et al. "HIV-1 Entry—An Expanding Portal for Drug Discovery" DDT, vol. 5, No. 5, pp. 183-194 (2000).

(Continued)

*Primary Examiner* — Zohreh Fay
(74) *Attorney, Agent, or Firm* — Wilmer Cutler Pickering Hale and Dorr LLP

(57) ABSTRACT

The present invention is directed to methods of inhibiting STDs by topically administering suramin or a derivative thereof to actual or potential sites of infection, and methods of preventing pregnancy by topically applying suramin or a derivative thereof intravaginally. Suramin compositions that include an antimicrobial agent and/or a sperm-function inhibitor are also provided and may advantageously be used in the methods of the invention. A method of simultaneously inhibiting STDs and preventing pregnancy is also provided. Devices impregnated or coated with the topical suramin compositions are further disclosed and may be used to apply the compositions described herein.

9 Claims, 13 Drawing Sheets

(56) References Cited

OTHER PUBLICATIONS

Bourinbaiar et al. "Comparative in Vitro Study of Contraceptive Agents With Anti-HIV Activity: Gramicidin, Nonoxynol-9, and Gossypol" Contraception, vol. 49, pp. 131-137 (1994).

Bourne et al. "The Topical Microbicide PRO 2000 Protects Against Genital Herpes Infection in a Mouse Model" The Journal of Infectious Diseases, vol. 180, pp. 203-205 (1990).

Broder et al. "Effects of Suramin on HTLV-III/LAVA Infection Presenting as Kaposi's Sarcoma or AISA-Related Complex: Clinical Pharmacology and Suppression of Virus Replication in Vivo." The Lancet, vol. 2 (5456), p. 627-630 (1985).

Bulut et al., Assessing the Acceptability, Service Delivery Requirements, and Use-Effectiveness of the Diaphragm in Colombia, Philippines, and Turkey, Contraception, vol. 63, pp. 267-275 (2001).

Burkman et al. "The Hemizona Assay (HZA): Development of a Diagnostic Test for the Binding of Human Spermatozoa to the Human Hermizona Pellucida to Predict Fertilization Potential." Fertility and Sterility, vol. 49, No. 4, p. 688-697 (Apr. 1988).

Campbell, et al. "Lipid Rafts and HIV-1: From Viral Entry to Assembly of Progeny Virions" Journal of Clinical Virology, vol. 22, pp. 217-227 (2001).

Chantler "New and Existing Spermicides With Virucidal Properties" Heterosexual Transmission of AIDS, pp. 303-310 (1990).

Cooper et al. "*Chlamydia trachomatis* Infection of Human Fallopian Tube Organ Cultures." Journal of General Microbiology, vol. 136, p. 1109-1115 (1990).

Corner, et al. "C31G, a New Agent for Oral Use with Potent Antimicrobial and Antiadherence Properties" Antimicrobial Agents and Chemotherapy, vol. 32, No. 3, pp. 350-353 (1988).

Cummins et al. "A Test of the Human Sperm Acrosome Reaction Following Ionophore Challenge: Relationship to Fertility and Other Seminal Parameters." Journal of Andrology, vol. 12, No. 2, p. 98-103 (Mar./Apr. 1991).

Darroch et al. "Women's Interest in Vaginal Microbicides" Family Planning Perspectives, vol. 31, No. 1, pp. 16-23 (1999).

De Clercq "Current Lead Natural Products for the Chemotherapy of Human Immunodeficiency Virus (HIV) Infection" Rega Institute for Medical Research, pp. 323-349 (2000).

De Clercq "Suramin: A Potent Inhibitor of the Reverse Transcriptase of RNA Tumor Viruses" Cancer Letters, vol. 8, pp. 9-22 (1979).

Dell et al. "The Glycobiology of Gametes and Fertilization" Biochimeca et Biophysica Acta 1473, pp. 196-205 (1999).

Edelstein "Studies on the in Vitro Spermicidal Activity of Synthetic Magainins" Fertility and Sterility, vol. 55, No. 3 pp. 647-649 (1991).

European International Search Report for International Application No. PCT/US1998/14891, dated Oct. 16, 1998.

Feldblum et al. "Self-reported Discomfort Associated with Use of Different Nonoxynol-9 Spermicides." Genitourin Med., vol. 72, No. 6, p. 451-452 (1996).

Fichorova et al. "The Molecular Basis of Nonoxynol-9-Induced Vaginal Inflammation and Its Possible Relevance to Human Immunodeficiency Virus Type 1 Transmission." The Journal of Infectious Diseases, vol. 184, No. 4, p. 418-428 (2001).

Fihn et al. "Association Between Use of Spermicide-Coated Condoms and *Escherichia coli* Urinary Tract Infection in Young Women." American Journal of Epidemiology, vol. 144, No. 5, p. 512-520 (1996).

Gagliardi et al. "Antiagniogenic and Antiproliferative Activity of Suramin Analogues." Cancer Chemother Pharmacol., vol. 41, p. 117-124 (1998).

Garg et al. "Properties of a New Acid-Buffering Bioadhesive Vaginal Formulation (ACIDFORM)" Contraception, vol. 64 pp. 67-75 (2001).

Garson, J.A. et al: "Suramin blocks hepatitis C binding to human hepatoma cells in vitro." Journal of Medical Virology, vol. 57, No. 3, pp. 238-242. XP002479690 (1999).

Geiger et al. "Risk Factors for Vulvovaginal Candidiasis: A Case-Control Study Among University Students." Epidemiology, vol. 7, No. 2, p. 182-187 (1996).

Herold et al. "Differences in the Susceptibility of *Herpes simplex* Virus Types I and 2 to Modified Heparin Compounds Suggest Serotype Differences in Viral Entry." Journal of Virology, vol. 70, No. 6, p. 3461-3469 (1996).

Herold et al. "Sulfated Carbohydrate Compounds Prevent Microbial Adherence by Sexually Transmitted Disease Pathogens" Antimicrobial Agents and Chemotherapy, vol. 41, No. 12, pp. 2776-2780 (1997).

Herold et al., "Poly(Sodium 4-Styrene Sulfonate): An Effective Candidate Topical Antimicrobial for the Prevention of Sexually Transmitted Diseases," The Journal of Infectious Diseases, vol. 181, pp. 770-773 (2000).

Hira et al. "Condom and Nonoxynol-9 Use and the Incidence of HIV Infection in Serodiscordant Couples in Zambia." International Journal of STD & AIDS, vol. 8, p. 243-250 (1997).

Hu et al. "Siminan Immunodeficiency Virus Rapidly Penetrates the Cervicovaginal Mucosa After Intravaginal Inoculation and Infects Intraepithelia Dendritic Cells." Journal of Virology, vol. 74, No. 13, p. 6087-6095 (Jul. 2000).

International Search Report for International Application No. PCT/US2003/009127, mailed May 12, 2004.

Jan et al. "Synthesis of Dual Function (5R,6R)- and (5S,6S)-5bromo-6-methoxy-5,6-kihydro-AZT-5-(para-bromophenyl methoxyalaninyl phosphate) as Novel Spermicidal and Anti-HIV Agent" Antiviral Chemistry & Chemotherapy, vol. 10, pp. 39-46 (1999).

Jentsch et al. "Inhibition of Human Immunodeficiency Virus Type I Reverse Transcriptase by Suramin-related Compounds." J. Gen. Virol. vol. 68, p. 2183-2192 (1987).

Jeyendran et al. "Development of an Assay to Assess the Functional Integrity of the Human Sperm Membrane and its Relationship to Other Semen Characteristics." J. Reprod. Fert., vol. 70, p. 219-228 (1984).

Jones et al. "Inhibition of sperm-zola binding by suramin, a potential 'lead' compound for design of new anti-fertility agent," Molecular Human Reproduction, vol. 2, No. 8, pp. 597-605 (1996).

Koomey "Implications of Molecular Contacts and Signaling Initiated by Neisseria Gonorrhoeae" Current Opinion in Microbiology, vol. 4, pp. 53-57 (2001).

Kreiss, et al. "Efficacy of Nonoxynol 9 Contraceptive Sponge Use in Preventing Heterosexual Acquisition of HIV in Nairobi Prostitutes" JAMA, vol. 268, No. 4, pp. 477-482 (1992).

Leon-Ponte et al., "Immunogenetics of HTLV-II Endemic Venezuelan Amerindian Populations," XIII International AIDS Conference, pp. 9-13 (2000).

Mahmoud et al., "Antichlamydial Activity of Vaginal Secretion," Am. J. Obstet. Gynecol., vol. 172, No. 4, part 1, pp. 1268-1272 (1995).

Martin et al. "Safety of Nonoxynol-0 Vaginal Gel in Kenyan Prostitutes." Sexually Transmitted Diseases, vol. 24, No. 5, p. 279-283 (May 1997).

Mauck et al. "Recommendations for the Clinical Development of Topical Microbicides: An Update" AIDS, vol. 15, pp. 587-868 (2001).

Mitsuya, et al. "Suramin Protection of T Cells in Vitro Against Infectivity and Cytopathic Effect of HTLV-II." Science, vol. 226 (4671), p. 172-174 (Oct. 12, 1984).

Nakajima et al. "Suramin: A Potent Inhibitor of Melanoma Heparanase and Invasion." The Journal of Biological Chemistry, vol. 266, No. 15, p. 9661-9666 (1991).

Neurath "Microbicide for Prevention of Sexually Transmitted Diseases Using Pharmaceutical Excipient" AIDS Patients Care and STDs, vol. 14, No. 4, pp. 215-219 (2000).

Neyts, J. et al: "Effect of Polyanionic compounds on intracutaneous and intravaginal herpes virus infection in mice etc." Journal of Acquired Immune Deficiency Syndromes and Humanretrovirology, Lippincot-Raven, vol. 10, pp. 8-12 (1995).

Nickel et al., "Potential Filarcides," Arzneim-Forsch, vol. 36, pp. 1153-1157 (1986).

Olmsted et al. "The Rate At Which Human Sperm Are Immobilized and Killed by Mild Acidity" Fertility and Sterility, vol. 73, No. 4, pp. 687-693 (2000).

PCT Notification of Transmittal of International Preliminary Examination Report for International Application No. PCT/US2003/09127 dated Jul. 7, 2004.

Phillips et al. "An Assay for HIV Infection of Cultured Human Cervix-Derived Cells." Journal of Virological Methods, vol. 52, p. 1-13 (1995).

Pisell, TL, et al. "Spectrum of cdk inhibitor activity against HIV-1 replication among various models of chronic and latent infection," Antiviral Chemistry and Chemotherapy, vol. 12 (Supp. 1), pp. 33-41 (2001).

Reissig et al. "A Modified Colorimetric Method for the Estimation of N-Acetylamino Sugars." J. Biol. Chem. pp. 959-966 (1955).

Risso "Leukocyte Antimicrobial Peptides: Multifunctional Effector Molecules of Innate Immunity" Journal of Leukocyte Biology, vol. 68, pp. 785-792 (2000).

Roddy et al. "A Controlled Trial of Nonoxynol 9 Film to Reduce Male to Female Transmission of Sexually Transmitted Diseases." The New England Journal of Medicine, vol. 339, No. 8, p. 504-510 (1998).

Rowe et al. "Nonoxynol-9 Fails to Protect Against HIV-1." The Lancet, vol. 349, p. 1074 (1997).

Sander et al. "A Practical Method for Testing Spermicidal Action of Chemical Contraceptives." Human Fertility, vol. 6, No. 5. p. 134-153 (1941).

Savle et al. "Acylcarnitine Analogues As Topical, Microbicidal Spermicides" Bioorganic & Medicinal Chemistry Letters 9, pp. 2545-2548 (1999).

Schang et al. "Pharmaceutical Cyclin-Dependent Kinase Inhibitors Inhibit Replication of Wild-Type and Drug Resistant Strains of *Herpes simplex* Virus and Human Immunodeficiency Virus Type 1 by Targeting Cellular, not Viral Proteins." Journal of Virology, vol. 76, No. 15, pp. 7874-7882 (Aug. 2002).

Shenoy et al. "Selective Interactions of the Human Immunodeficiency Virus-Inactivating Protein Cyanovirin-N. with High-Mannose Oligosaccharides on jp120 and Other Glycoproteins" The Journal of Pharmacology and Experimental Therapeutics, vol. 297, No. 2, pp. 704-710 (2001).

Stafford et al. "A Placebo-Controlled, Double-Blind Prospective Study in Healthy Female Volunteers of Dextrin Sulphate Gell: A Novel Potential Intravaginal Virucide" JAIDS, vol. 14, No. 3, pp. 1-8 (1996).

Stafford et al. "Safety Study of Nononxynol-9 as a Vaginal Microbicide: Evidence of Adverse Effects." Journal of Acquired Immune Deficiency Syndromes and Human Retrovirology, vol. 17, No. 4, p. 327-331 (1998).

Stephens et al. "*Chlamydia* Outer Membrane Protein Discovery Using Genomics" Current Opinion in Microbiology, vol. 4, pp. 16-20 (2001).

Stephenson "Widely Used Spermicide May Increase, Not Decrease, Risk of HIV Transmission" JAMA, vol. 284, No. 8, p. 949 (2000).

Supplementary European Search Report based on International Application No. PCT/US0309127, dated May 26, 2008.

Tokunaga et al. "Antibacterial Activity of Bactenecin 5 Fragments and Their Interaction with Phospholipid Membranes" Journal of Peptide Science, vol. 7, pp. 297-304 (2001).

Ugolini, et al. "HIV-1 Attachment: Another Look" Trends in Microbiology, vol. 7, No. 4, pp. 144-149 (1999).

Van Damme et al. "Effectiveness of COL-1492, a Nonoxynol-9 Vaginal Gel, on HIV-1 Transmission in Female Sex Workers: A Randomized Controlled Trial." The Lancet, vol. 360, p. 971-977 (2002).

Vanham et al. "Modeling HIV Transfer Between Dendritic Cells and T Cells: Importance of HIV Phenotype, Dendritic Cell-T Cell Contact and T-cell Activation." AIDS 2000, vol. 14, p. 2299-2311 (2000).

Venkata Rami Reddy, et al. "Spermicidal Activity of Magainins: in Vitro and in Vivo Studies" Contraception, vol. 53, pp. 205-210 (1996).

Wang et al. "Inhibition of Human Immunodeficiency Virus Type 1 Transcription by Chemical Cyclin-Dependent Kinase Inhibitors," Journal of Virology, vol. 75, No. 16, pp. 7266-7279 (Aug. 2001).

Who Laboratory Manual for the Examination of Human Semen and Sperm-Cervical Mucous Interaction, 4th Ed., WHO Organization, Cambridge University Press, p. 30-33 (1999).

Yanigimachi et al. "The Use of Zona-Free Animal Ova as a Test-System for the Assessment of the Fertilizing Capacity of Human Spermatoza." Biology of Reproduction, vol. 15, p. 471-476 (1976).

Zheng, et al. "Effects of $H_2O_2$-Producing *Lactobacilli* on Neisseria Gonorrhea Growth and Catalase Activity" The Journal of Infectious Diseases, vol. 170, pp. 1209-1215 (1994).

Pauwels, R. et al., "Development of Vaginal Microbicides for the Prevention of Heterosexual Transmission of HIV," Journal of Acquired Immune Deficiency Syndromes and Human Retrovirology, vol. 11, No. 3, 1996; pp. 211-221.

Examination Report mailed by European Patent Office on Apr. 5, 2011 for corresponding European Patent Application No. 03721455.8.

Doncel, "Chemical Vaginal Contraceptives: Preclinical Evaluation," Barrier Contraceptives, Current Status and Future Prospects, Proceedings of the Fourth Contraceptive Research and Development Program International Workshop, Santo Domingo, Dominican Republic, Mar. 22-25, 1993, Chapter 10, pp. 147-162.

Firsching-Hauck, et al., "Preclinical Report: Angiostatic Effects of Suramin Analogs in Vitro," Anti-Cancer Drugs, 2000, vol. 11, pp. 69-77.

* cited by examiner

SURAMIN AND DERIVATIVES THEREOF AS TOPICAL MICROBICIDE AND CONTRACEPTIVE

CROSS-REFERENCE TO RELATED APPLICATIONS

The present application is a divisional of U.S. patent application Ser. No. 10/508,566 filed on Mar. 11, 2005, now U.S. Pat. No. 7,476,693, which is a U.S. National Phase Application Under 35 U.S.C. §371 of International Patent Application No. PCT/US03/09127, filed Mar. 26, 2003, which claims the benefit of U.S. Provisional Application No. 60/367,273 filed Mar. 26, 2002.

STATEMENT REGARDING FEDERALLY SPONSORED RESEARCH OR DEVELOPMENT

This invention was made with government support under grant number HRN-A-00-98-00020-00 awarded by the Contraceptive Research and Development (CONRAD) Program, established as a cooperative agreement between the U.S. Agency for International Development (USAID) and the Eastern Virginia Medical School (EVMS). The government has certain rights in the invention.

BACKGROUND OF THE INVENTION

The invention generally relates to suramin and its derivatives in topical formulations and their use as microbicidal contraceptives for the prevention of sexually transmitted diseases (STD) and conception. According to the present invention, it has been found herein that suramin and its derivatives display potent activity against STD pathogens and has displayed antisperm activity, and alone or in combination with other sperm-function inhibitors, including spermicides, and/or other antimicrobials, including antivirals, they constitute effective vaginal contraceptive microbicides.

The increasing prevalence of STD is a serious public health problem affecting both developed and less-developed countries. In the latter, the acquired immune deficiency syndrome (AIDS) epidemic is taking a devastating toll in human lives. Constrained by lack of money, overpopulation and cultural habits that make condoms unpopular, these countries see a dramatic increase in the number of human immunodeficiency virus (HIV)-infected people, in some cases reaching one third of the population of reproductive age. There is an urgent need to develop safe, prophylactic, female-controlled agents that are effective against sexually transmitted pathogens, particularly HIV, and conception.

Nonoxynol-9 (N-9), a nonionic surfactant, is the only FDA-approved spermicide currently in the U.S. market. Other surfactants, such as benzalkonium chloride, are available as part of spermicidal preparations in Canada and Europe. Due to their effects on lipids, these surfactants display anti-HIV activity in vitro, disrupting the viral envelope and inactivating the virus. Unfortunately, as it has clearly been demonstrated for N-9, these surfactants alone do not appear to confer significant protection in vivo. Several clinical trials with N-9 have shown lack of reduction in the incidence of HIV infection (Rowe, Lancet., 349: 1074 1997; Hira et al., Int J. STD AIDS., 8(4) 243-50 1997; Martin et al., Sex. Transm. Dis., 24(5): 279-283, 1997; Roddy et al., N. Engl. J. Med., 339(8): 504-10 1998; Van Damme et al., Lancet., 360 (9338): 971-7 2002). In fact, it has been demonstrated that N-9 actually increases the risk of genital inflammation (Stafford et al., J. Acquir Immune Defic Syndr. Hum. Retrovirol. 17(4): 327-31 1998), urinary tract infections (Fihn et al., Am. J. Epidemiol, 144(5): 512-20 1996), vulvovaginal candidiasis (Geiger and Foxman, Epidemiology., 7(2): 182-7 1996) and genital ulcers (Feldblum, Genitourin Med., 72(6): 451-2 1996). A recent study (Fichorova et al., J. Infect. Dis., 184(4): 418-28 2001) reveals that N-9 is cytotoxic for the vaginal epithelium and induces the release of proinflammatory cytokines which, in turn, recruit immune cells that are targets for HIV, thus facilitating its tissue invasion.

For these reasons, there is a continuing need to develop a topical formulation that is harmless to mucosae and the mucosal microflora, effective against HIV and other STD pathogens such as Herpes simplex virus (HSV), Cytomegalovirus (CMV), *Neisseria gonorrhoeae* (NG), and *Chlamydia trachomatis* (CT), and at the same time, offers contraceptive protection.

SUMMARY OF THE INVENTION

It has been discovered that compositions that include suramin or a derivative thereof are effective as a contraceptive and in inhibiting transmission of sexually transmitted diseases. Accordingly, methods of inhibiting transmission of sexually transmitted diseases and methods of contraception are provided. Compositions that include suramin or a derivative thereof, and devices coated or impregnated with such compositions are also provided herein.

In a first aspect of the invention, methods of inhibiting transmission of sexually transmitted diseases are provided. In one form, a method includes topically, preferably vaginally, applying suramin or a derivative thereof. In certain forms of the invention, suramin may be co-administered in a composition with one or more antimicrobial agents.

In a second aspect of the invention, methods of contraception are provided. In one embodiment, a method includes administering to the vagina an amount of suramin or a derivative thereof effective to inhibit sperm-egg fertilization, and thus prevent pregnancy. In certain embodiments, suramin may be co-administered with one or more antimicrobial agents and/or sperm-function inhibitors.

In a third aspect of the invention, topical compositions are provided that may be advantageously used to inhibit transmission of sexually transmitted diseases and inhibit sperm-egg fertilization. In one embodiment, a composition includes a pharmaceutically-acceptable carrier and an amount of a surfactant and either suramin or a derivative thereof effective to inhibit transmission of sexually transmitted diseases and inhibit sperm-egg fertilization.

In a fourth aspect of the invention, devices for administering suramin to the vagina or uterus are provided. In one embodiment, a device includes a solid support adapted to be inserted into the vagina. The support is advantageously impregnated with or coated with a composition that includes a surfactant and either suramin or a derivative thereof.

In a fifth aspect of the invention, methods for simultaneously inhibiting sexually transmitted infections and inhibiting sperm-egg fertilization are provided. In one form, a method includes administering to a female mammal intravaginally, to the cervix or to the uterus, a composition that includes suramin in an amount effective to inhibit sexually transmitted infections and sperm-egg fertilization. The sexually transmitted infections may be caused by a microorganism, such as *Neisseria gonorrhoeae, Chlamydia trachomatis, Treponema pallidum, Haemophilus ducreyi, Calymmatobacterium granulomatis, Mycoplasma genitalium, Ureaplasma urealyticum*, HIV-1, HIV-2, HTLV-1, herpes simplex virus type 1, herpes simplex virus type 2, Epstein-Barr virus, cytomegalovirus, human herpesvirus 6, varicella-zoster virus, human papillomaviruses, hepatitis A virus, hepatitis B virus, *Trichomona vaginalis*, and *Candida albicans*.

DESCRIPTION OF THE PREFERRED EMBODIMENTS

It has been found that suramin and derivatives thereof in a topical formulation have a combined effectiveness to inhibit transmission of STD infections and reduce the probability of sperm-egg fertilization (i.e., fertilization of an egg by sperm).

Applicants have found that the topical administration of suramin and derivatives thereof is effective to inhibit transmission of STDs and prevent pregnancy.

In a first aspect of the invention, methods of inhibiting transmission of sexually transmitted diseases are provided. In one form, a method includes topically applying or otherwise administering suramin or a derivative thereof, typically to a site of infection.

Figure 1:
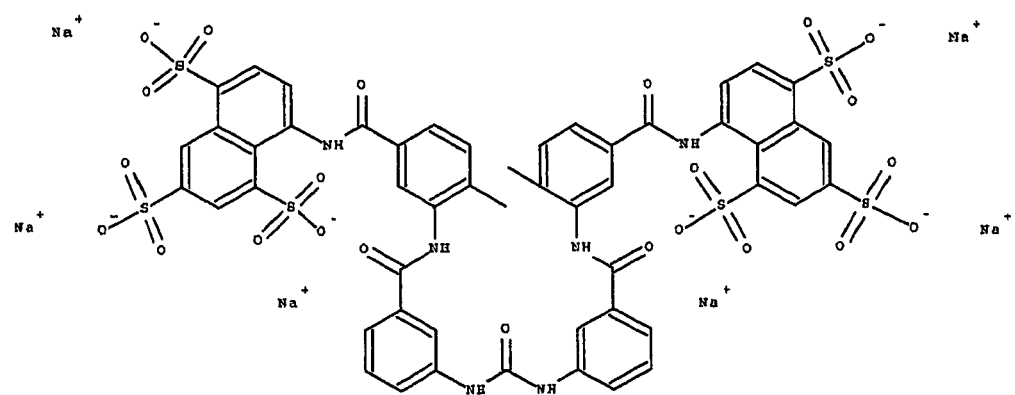
FIG. 1 depicts the hexasodium salt of suramin, 8,8'-(carbonyl bis(imino-3,1-phenylenecarbonylimino(4-methyl-3,1-phenylene)carbonylimino-))bis-1,3,5-naphthalene trisulfonic acid.

Suramin is a polysulfonated naphthyl urea having the chemical name 8,8'-(carbonyl bis(imino-3,1-phenylenecarbonylimino(4-methyl-3,1-phenylene) carbonylimino))bis-1, 3,5-naphthalene trisulfonic acid. The structure of the hexasodium salt of suramin is depicted in FIG. 1. Suramin is commercially available and is also known under the following chemical and trade names: Antrypol, Bayer 205, Fourneau 309, Germanin, Moranyl, Naganol, Naganin, Suramin, Naphuride Sodium. Suramin has been previously shown to inhibit in vivo activities of various growth factors and autoimmune and allergenic diseases (U.S. Pat. No. 5,158,940), possess potent reverse transcriptase (RT) inhibitory activity (Jentsch et al., J. Gen. Virol., 68: 2183-2192 1987), and antiproliferative activity (Nakajima et al., J. Biol. Chem., 266 (15): 9661-6 1991).

As used herein, "suramin" shall include both suramin and pharmaceutically acceptable salts thereof that are effective in inhibiting STD infections and inhibiting sperm-egg fertilization. Pharmaceutically acceptable salts, include, for example, alkaline metal, alkaline earth metal, other non-toxic metals, ammonium and substituted ammonium salts such as, but not limited to, the sodium, potassium, lithium, calcium, magnesium, aluminum, zinc, ammonium, trimethyl ammonium, triethyl ammonium, tetrabutyl ammonium, pyridinium and substituted pyridinium salts. Preferably, a hexasodium salt of suramin is employed.

"Derivatives" (analogues) of suramin are known in the art and include those described, for example, by Jentsch et al., J. Gen. Virol., 68: 2183-2192 (1987), and U.S. Pat. Nos. 5,173, 509 and 6,121,320, which are both herein incorporated by reference in their entirety. Other known suramin derivatives are described, for example, in U.S. Pat. No. 6,121,320, which describes NF110, NF032, NF201, NF023, and NF103 derivatives of suramin, and in Firsching-Hauck et al., Anticancer Drugs 11 (2): 69-77 (2000) and Gagliardi et al., Cancer Chemother. Pharmacol. 41(2): 117-24 (1998). The derivatives can be synthesized by methods known to the skilled artisan, including by the methods described in, for example, Nickel P et al., Arzneim.-Forsch. 36, 1153-1157 (1986).

It has unexpectedly been found that combining suramin or a derivative thereof with other active agents described herein leads to synergistic interactions. Accordingly, in yet another embodiment of the invention, the method described herein for inhibiting transmission of sexually transmitted diseases includes topically applying compositions that include suramin and one or more active agents. As defined herein, an active agent includes an antimicrobial agent, or other agent that displays anti-STD pathogen activity. The active agent may also be a sperm-function inhibitor that has the ability to inhibit the function of sperm, to otherwise inhibit fertilization of an egg by sperm and/or to otherwise prevent pregnancy, such as by killing and/or functionally inactivating sperm or by other effects on the activity of the sperm. The active agent may have at least dual functions, such as acting as a sperm-function inhibitor and as an antimicrobial agent.

The antimicrobial agent may be active against algae, bacteria, fungi, parasites (helminths, protozoa), viruses, and subviral agents. Accordingly, the antimicrobial agent may be an antibacterial, antifungal, antiviral, antiparasitic, and an antiprotozoal agent. The antimicrobial agent is preferably active against infectious diseases, such as sexually-transmitted diseases. Examples of microorganisms that cause such diseases (and the diseases caused by such microorganisms) include *Neisseria gonorrhoeae* (gonorrhea); *Chlamydia trachomatis* (chlamydia, lymphogranuloma venereum); *Treponema pallidum* (syphilis); *Haemophilus ducreyi* (chancroid); *Calymmatobacterium granulomatis* (donovanosis), *Mycoplasma genitalium, Ureaplasma urealyticum* (mycoplasmas); human immunodeficiency virus HIV-1 and HIV-2 (HIV, AIDS); HTLV-1 (T-lymphotrophic virus type 1); herpes simplex virus type 1 and type 2 (HSV-1 and HSV-2); Epstein-Barr virus; cytomegalovirus; human herpesvirus 6; varicella-zoster virus; human papillomaviruses (genital warts); hepatitis A virus, hepatitis B virus (viral hepatitis); *Trichomona vaginalis* (trichomoniasis); and yeasts, such as *Candida albicans* (vulvovaginal candidiasis). The antimicrobial agent may also be active against other diseases that are transmitted by contact with bodily fluids that may also be transmissible by sexual contact and are capable of being prevented by administration of the compositions according to this invention. Accordingly, the phrase, "sexually transmitted diseases (STDs)," is to be interpreted herein as including any disease that is capable of being transmitted in the course of sexual contact, whether or not the genital organs are the site of the resulting pathology.

Suitable antiviral agents include, for example, virus-inactivating agents such as the nonioinic, anionic and cationic surfactants discussed herein, and C31 G (amine oxide and alkyl betaine), polybiguanides, docosanol, acylcarnitine analogs, octyl glycerol, and antimicrobial peptides such as magainins, gramicidins, protegrins, and retrocyclins. Mild surfactants may advantageously be used as antiviral agents in the compositions described herein. In one embodiment, the suramin composition for inhibiting STD infection includes an antiviral surfactant that does not inhibit the STD-causing microorganism through the same mechanism as suramin. More preferably, the antiviral surfactant is sorbitan monolaurate. Other antiviral agents that may advantageously be utilized in the compositions described herein include nucleotide or nucleoside analogs, such as tenofovir, acyclovir, amantadine, didanosine, foscarnet, ganciclovir, ribavirin, vidarabine, zalcitabine, and zidovudine. Further antiviral agents that may be used include non-nucleoside reverse transcriptase inhibitors, such as UC-781 (thiocarboxanilide), pyridinones, TIBO, nevaripine, delavirdine, calanolide A, capravirine and efavirenz. From these reverse transcriptase inhibitors, agents and their analogs that have shown poor oral bioavailability are especially suitable for vaginal administration, in combination with suramin, to prevent sexual transmission of HIV. Other antiviral agents that may be used in combination with suramin are those in the category of HIV entry blockers, such as cyanovirin-N, clyclodextrins, carregeenans, sulfated or sulfonated polymers, mandelic acid condensation polymers, monoclonal antibodies, chemokine receptor antagonists such as TAK-779, SCH-C/D, and AMD-3100, and fusion inhibitors such as T-20 and 1249.

Suitable antibacterial agents include antibiotics, such as aminoglycosides, cephalosporins, including first, second and third generation cephalosporins; macrolides, including erythromycins, penicillins, including natural penicillins, penicillinase-resistant penicillins, aminopenicillins, extended spectrum penicillins; sulfonamides, tetracyclines, fluoroquinolones, metronidazole and urinary tract antiseptics.

Suitable antifungal agents include amphotericin B, nystatin, griseofulvin, flucytosine, fluconazole, potassium iodide, intraconazole, clortrimazole, miconazole, ketoconazole, and tolnaftate.

Suitable antiprotozoal agents include antimalarial agents, such as chloroquine, primaquine, pyrimethamine, quinine, fansidar, and mefloquine; amebicides, such as dioloxamide, emetine, iodoquinol, metronidazole, paromomycine and quinacrine; pentamidine isethionate, atovaquone, and eflornithine.

The suramin compositions of the present invention according to the methods described herein are administered or otherwise applied by topically delivering the composition, typically to a site of infection. The site of infection may be one where an infection is already present (an actual site of infection) or where an infection is likely to occur (a potential site of site of infection in or on an uninfected individual). Accordingly, the compositions may be topically delivered to the vulva, including the vaginal cavity, the penis and the ano-rectal and buccal cavities by contacting the skin or mucosae of the intended site or surrounding the intended site. The mucosal or skin surface may further include the perianal, and the lining of the anus. For example, in the case of inhibiting STD-infections, the suramin compositions of the present invention may be administered by being contacted with any potential or actual sites of infection, including the vaginal, ano-rectal or buccal cavities to prevent STD infection during intimate activity. When administered to the vaginal cavity, the compositions may also be applied to any portion of the uterus, including inside the uterus and on the cervix, including the mucosa and/or lining of the endo- and ecto-cervix. Moreover, when formulated as a lubricant, the compositions can be applied to external genitalia and internal mucosal surfaces to reduce microtrauma resulting from inadequate lubrication and will also prevent transmission of viable STD pathogens through traumatized, diseased or healthy skin or mucosa.

A dose of the pharmaceutical composition is preferably made up of one or more pharmaceutical dosage units. The selected dose may be administered to a mammal, for example, a human, by any known method of administering the dose, including the methods described herein, for example, as a suppository or gel to be applied to the vagina, rectum or uterus. For example, the suramin compositions may be delivered intravaginally by applying as a lubricant, for example, on a device, including a sponge, cervical cap, tampon, diaphragm, or intrauterine device or by applying the composition as a suppository, douche, ovule, gel, or other controlled delivery device. Although placing the compositions on a condom can result in transfer of some of the compositions to a mucosal surface and provide a degree of protection for such surfaces, the primary benefits of such an application include protection of the condom wearer. The suramin compositions may be applied to any portion of the uterus by an intrauterine delivery device, such as those intrauterine devices (IUDs) known to those skilled in the art. Applicators known to the art, such as those currently used commercially to deliver spermicidal gels or anti-yeast compounds, may also be used to deliver the compositions intravaginally.

A STD-infection inhibitory or otherwise preventative or effective amount of the suramin composition is typically administered. This amount is intended to mean that amount of suramin, when administered to a mammal in need thereof, that is sufficient to effect inhibition of transmission of STD infections. In other words, the dose is that effective to prevent STD infection at the site of entry or to prevent the replication of the STD-causing microorganism. In the case of inhibiting transmission of STD infections, the effective amount of suramin may vary depending upon factors such as the STD-causing microorganism intended to be inhibited by blocking its entry or ceasing its replication at the site of infection. For example, the suramin compositions of the present invention are suitably formulated to inhibit human immunodeficiency virus (HIV) (including, but not limited to, HIV-1 and HIV-2), Herpes simplex virus (HSV), Cytomegalovirus (CMV), *Neisseria gonorrhoeae* (NG), and *Chlamydia trachomatis* (CT). Preferably, the effective amount of suramin is that which is effective to inhibit transmission of any of the potential STD-causing microbes known to the art and described herein. Although these amounts may vary, suramin is typically applied in an amount of from about 0.1% (1 mg of suramin per 1 gram of formulation) to about 30% (300 mg/g), preferably about 1% (10 mg/g) to about 5% (50 mg/g); or in a way in which the delivery system releases enough suramin to maintain these percent concentrations in weight over volume. When present in a composition with an antimicrobial agent, the amount of suramin in the composition applied will also vary with respect to the specific antimicrobial agent used and may be readily determined by the skilled artisan. The amount of the antimicrobial agent in the composition will vary depending on, for example, the nature of the disease involved and the amount of suramin in the composition and may also be readily determined by the skilled artisan. These amounts may be administered to an individual with a STD or to an individual who intends to have sexual contact with an individual with a STD.

"Inhibiting" or "inhibit" as referenced in the methods of the present invention is intended to mean at least the reduction in incidence or prevalence of the occurrence of the specified activity relative to an untreated individual. These terms may include the prophylactic or preventative treatment in a mammal or the reduction in the incidence of a condition relative to untreated mammals. The "inhibition" of transmitting STD infection refers to the reduced transmission of STD infection as a result of treatment of the individual prior to, or immediately after, intimate contact relative to untreated individuals. In such case, and not being limited by any particular mechanism of action, the inhibition of transmitting STDs may be caused by neutralizing the microorganism causing the STD infection at the site of infection or by preventing the replication of the microorganism at the site of infection. The inhibition of the STD infection is between at least two people in sufficient contact with each other to, contract the STD infection. For example, the inhibition of the STD infection can be between two persons involved in sexual contact or between a mother and child (vertical transmission).

A wide variety of STD infections may be inhibited according to the methods of the present invention. For example, suramin, and the compositions described herein, can be used against microorganisms within the categories of algae, bacteria, fungi, parasites (helminths, protozoa), viruses, and subviral agents. For example, suramin compositions may be applied according to the methods of the present invention to inhibit transmission of diseases caused by various microorganisms, including *Neisseria gonorrhoeae* (gonorrhea); *Chlamydia trachomatis* (chlamydia, lymphogranuloma venereum); *Treponema pallidum* (syphilis); *Haemophilus ducreyi* (chancroid); *Calymmatobacterium granulomatis* (donovanosis); *Mycoplasma genitalium*, *Ureaplasma urealyticum* (mycoplasmas); human immunodeficiency virus HIV-1 and HIV-2 (HIV, AIDS); HTLV-1 (T-lymphotrophic virus type 1); herpes simplex virus type 1 and type 2 (HSV-1 and HSV-2); Epstein-Barr virus; cytomegalovirus; human herpesvirus 6; varicella-zoster virus; human papillomaviruses (genital warts); hepatitis A virus, hepatitis B virus (viral hepatitis); *Trichomona vaginalis* (trichomoniasis); and yeasts, such as *Candida albicans* (vulvovaginal candidiasis). The diseases caused by such microorganisms are shown in parenthesis above.

In yet other forms of the invention, the STD infections may be caused by bacteria. Examples of such bacteria include *Neisseria gonorrhoeae, Chlamydia trachomatis, Treponema pallidum, Haemophilus ducreyi, Calymmatobacterium granulomatis, Mycoplasma genitalium*, and *Ureaplasma urealyticum*. In yet other embodiments, the STD infections may be caused by a virus, including HIV-1, HIV-2, HTLV-1, herpes simplex virus type 1, herpes simplex virus type 2, Epstein-Barr virus, cytomegalovirus, human herpesvirus 6, varicella-zoster virus, human papillomaviruses, hepatitis A virus, and hepatitis B virus. In other embodiments of the invention, the STD infections may be caused by a virus, such as HTLV-1, Epstein-Barr virus, varicella-zoster virus, human papillomaviruses, hepatitis A virus, and hepatitis B virus. In further embodiments, the STD infection may be caused by *Candida albicans* and *Trichomona vaginalis*.

In yet another aspect of the invention, methods of contraception, or otherwise preventing pregnancy, are provided. In one form, a method includes administering to the vagina an amount of suramin or derivative thereof effective to inhibit sperm-egg fertilization and otherwise prevent pregnancy. In other embodiments of the invention, the suramin or derivative thereof may be combined with a different sperm-function inhibitor, as such a combination has been found herein to exert synergistic effects with respect to contraception. Compositions that include suramin and a derivative thereof, optionally in combination with the active agents described herein, are also envisioned for use in the methods described herein.

The sperm-function inhibitor that increases the contraceptive properties of suramin may be selected from, for example, surfactants, including nonionic surfactants, cationic surfactants, and anionic surfactants; spermicides, such as nonoxynol-9 (α-(4-Nonylphenyl)-ω-hydroxynona(oxyethylene); other sperm-inactivators such as sulfated or sulfonated polymers such as polystyrene sulfonate, mandelic acid condensation polymers, cyclodextrins; antimicrobial peptides such as gramicidins, magainins, indolicidin, and melittin; and acid-buffering compositions, such as BufferGel and AcidForm. Nonionic surfactants include, for example, sorbitan monolaurate, nonylphenoxypolyethoxy ethanol, p-diisobutyphenoxypolyethoxy ethanol, polyoxyethylene (10) oleyl ether and onyx-ol. Suitable anionic surfactants include, without limitation, sodium alkyl sulfonates and the sodium alkylbenzene sulfonates. Cationic surfactants include, for example, the quaternary ammonium surfactants, such as cetyl pyrimidinium chloride and benzalkonium chlorides. Zwitterionic surfactants such as acylcarnitine analogs and C31G are especially suitable for their mild skin and mucosal irritation properties.

In the case of inhibiting sperm-oocyte fertilization, or otherwise preventing pregnancy, the suramin compositions of the present invention are intravaginally applied either directly or indirectly. For example, the suramin compositions may be delivered intravaginally by applying as a lubricant, for example, on a condom or other device, including a sponge, cervical cap, tampon, diaphragm, or intrauterine device or by applying the composition as a suppository, douche, ovule, gel, or other controlled delivery device. The suramin compositions may be applied to any portion of the uterus by an intrauterine delivery device, such as those intrauterine devices (IUDs) known to those skilled in the art. Applicators known to the art, such as those currently used commercially to deliver spermicidal gels or anti-yeast compounds, may also be used to deliver the compositions.

An effective amount of the suramin compositions is typically administered. This effective amount, in the context of the methods of contraception described herein, is intended to mean that amount of suramin, when administered to a mammal in need thereof, sufficient to effect inhibition of sperm-egg fertilization and embryo formation. In the case of its contraceptive properties, the effective amount of suramin is that amount effective to decrease the possibility of sperm-egg fertilization, either by blocking entry of sperm into the egg, inhibiting sperm-fertilizing capabilities or by other methods. This amount of suramin may be readily determined by one of skill in the art. For example, the suramin may be present, in an effective amount, preferably in an amount of from about 1 to about 300 mg per gram of composition, preferably about 5 to about 100 mg/g, or in the range of 0.0001-90%, preferably about 0.01 to about 30% or about 0.5% to about 10% by weight of the composition. Higher and lower amounts may also be effectively employed in the practices of this invention.

Moreover, the "inhibition" of sperm-egg fertilization refers to the reduced occurrence of conception, i.e., sperm-egg fertilization, resulting in pregnancy relative to untreated individuals. In such case, the suramin may act in a number of different ways. For example, it may inhibit fertilization by blocking sperm receptors to the zona pellucida. Alternatively, it may inhibit hyaluronidase or other sperm-enzyme interactions required for fertilization. It may also agglutinate sperm, impeding normal ascent or transport through the female genital tract. Whatever the mechanism, and not being limited by any particular theory of the mechanism of action of the compositions described herein, the inhibition of sperm-egg fertilization results in an effective contraceptive property for the suramin topical pharmaceutical compositions of the present invention.

The compositions used in the methods described herein may include other agents that do not negatively impact or otherwise affect the microbicidal and/or contraceptive effectiveness of the components of the composition, including antimicrobial agents, sperm-function inhibitors, suramin or derivatives of suramin. For example, solid, liquid or a mixture of solid and liquid pharmaceutically acceptable carriers, diluents, vehicles, or excipients may be employed in the pharmaceutical compositions. Suitable physiologically acceptable, substantially inert carriers include water, a polyethylene glycol, mineral oil or petrolatum, propylene glycol, hydroxyethylcellulose, carboxymethyl cellulose, cellulosic derivatives, polycarboxylic acids, linked polyacrylic acids, such as carbopols; and other polymers such as poly(lysine), poly (glutamic acid), poly(maleic acid), poly(lactic acid), thermal polyaspartate, and aliphatic-aromatic resin; glycerin, starch, lactose, calcium sulphate dihydrate, terra alba, sucrose, talc, gelatin, pectin, acacia, magnesium stearate, stearic acid, syrup, peanut oil, olive oil, saline solution, and the like.

The pharmaceutical compositions described herein useful in the methods of the present invention may further include diluents, fillers, binding agents, moisturizing agents, preservatives, acids, and other elements known to those skilled in the art. For example, suitable preservatives are well known in the art, and include, for example, methyl paraben, propyl paraben, butyl paraben, benzoic acid and benzyl alcohol.

The compositions used in the methods of the invention may be employed in any form suitable for topical application. For example, the compositions of this invention could be in various forms known to the art, including liquid form or in lotion form, either oil-in-water or water-in-oil emulsions, in aqueous gel compositions, in the form of foams, films, sprays, ointments, pessary, suppository, capsules, tablets, jellies, creams, liposomes or in other forms embedded in a matrix for the slow or controlled release of the biologically active material to the skin or surface onto which it has been applied or in contact. Preferably, the compositions of the present invention are aqueous compositions. Most preferably, the compositions are aqueous gel compositions.

In yet another aspect of the invention, methods for simultaneously inhibiting sexually transmitted diseases or infections and inhibiting sperm-egg fertilization are provided. The suramin compositions of the present invention are effective for simultaneously inhibiting mucosal entry of STD-causing microorganisms, including HIV, Herpes Simplex virus, Cytomegalovirus, *Chlamydia trachomatis* and *Neisseria gonorrhoeae*, as well as inhibiting sperm-egg fertilization in a female mammal. In such a case, the suramin composition is delivered intravaginally to a female mammal in a microbicidal contraceptive amount sufficient to inhibit sperm-egg fertilization in the female mammal and to inhibit STDs or infections. The inhibition of STD may occur by, for example, preventing STD-causing microorganisms from entering the cervico-vaginal mucosa and/or preventing such microorganisms to replicate and grow in the female mammal.

Reference will now be made to specific examples illustrating the methods, compositions and devices above. It is to be understood that the examples are provided to illustrate preferred embodiments and that no limitation of the scope of the invention is intended thereby.

Example 1

Anti-Sperm Activity

Sperm Immobilization

The Sander Cramer test was used to determine the effect on sperm immobilization as described in Sander F V and Cramer S D., Hum. Fertil. 6: 134-153 (1941). This test may be used to evaluate the sperm-immobilizing effectiveness of contraceptive compositions. Serial dilutions of each test composition were added to semen adjusted to a designated number, e.g., 60 million of motile sperm per milliliter at room temperature (i.e., 25° C.). The end point is the greatest dilution at which all of the sperm are immobilized within 20 seconds. Results are expressed as minimum effective concentration in milligrams per milliliter.

Figure 2:
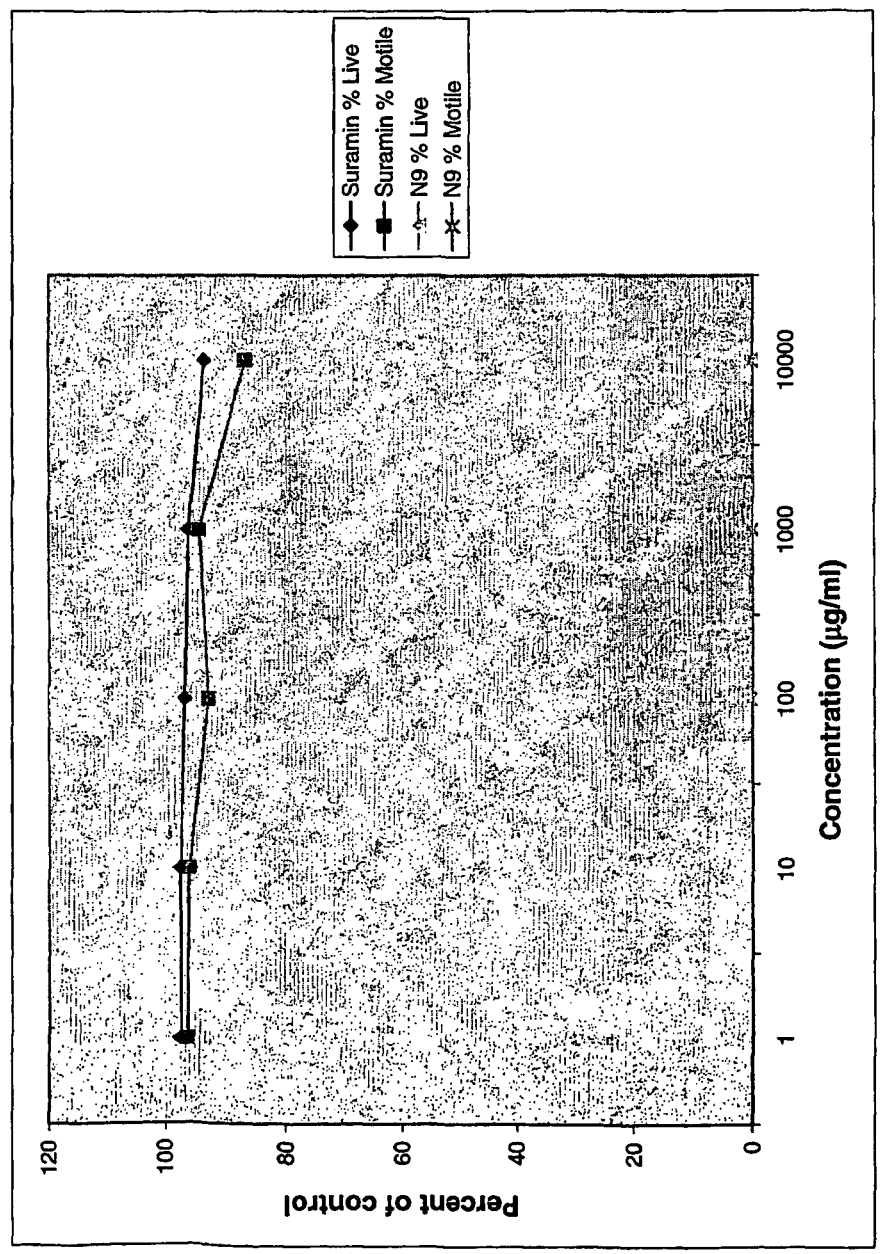
FIG. 2 is a graph depicting sperm motility and viability as a function of indicated concentrations of suramin and nonoxynol-9 as more fully described in Example 1.

Suramin showed no significant sperm-immobilizing activity at 20 mg/mL. Additionally, all spermatozoa from samples were motile when the experiment was conducted with 10 and 5 mg/mL suramin sodium. In more detailed dose-response studies using 1 log-fold concentrations (1-10,000 µg/mL) or 2-fold serial dilutions (5-0.07 mM) and sperm progressive motility and membrane integrity as endpoints, suramin sodium did not show significant differences with its solvent control, i.e., it induced no alteration of sperm progressive movement and viability (FIG. 2). Conversely, the commercial spermicide nonoxynol-9 (N-9), run in parallel, displayed its known sperm-immobilizing effects. In a time-dependent study at suboptimal doses, unlike N-9, suramin sodium showed no alteration of sperm motility even after prolonged incubation time (e.g., 30 min.). At 1 mM, no significant changes in sperm motion parameters were detected by CASA (Computer-Assisted Semen Analysis) as described, for example, in WHO laboratory manual for the examination of human semen and sperm-cervical mucus interaction, 4th ed., WHO Organization, Cambridge University Press, pp. 30-33, 1999. Even at higher concentrations (e.g., 7.5 mg/mL), sperm motion characteristics did not appear to be significantly different from those of the control (solvent-treated) sperm.

Cervical Mucus Penetration Effects

Bovine cervical mucus was obtained from Humagen (Charlottesville, Va.) in the form of prepackaged flat capillary tubes (Penetrak®), kept frozen and thawed right prior to the experiment. The Modified One End Test (MOET) [(described in Doncel G. F., in "Barrier Contraceptives", Wiley-Liss, Mauck C. K. et al. eds., pp. 147-162 (1994)] was used to determine the effect of compounds, such as suramin sodium described herein, on sperm penetration in cervical mucus. Each of the test compositions containing the compound to be tested were diluted in a saline solution, i.e., at 9 grams of NaCl per liter of water. Tubes of cervical mucus were broken open. The open end was placed in a container containing the test compound in saline. The test compound was allowed to diffuse for 30 minutes through the tube. A semen sample, obtained from normal healthy donors, was then diluted with a buffer solution to 60 million motile sperm per milliliter and mixed with the test compound sample (i.e., suramin sodium). The tube containing the test compound sample was then re-inserted into the container containing the mixed solution and stored in an incubator at 37° C. in an atmosphere of 5 percent carbon dioxide in air for 60 minutes. The container and tube were then removed from the incubator and the tube was visually analyzed under a microscope for the migration of motile vanguard sperm through the tube. The results are expressed as percentage of migration as compared to control samples. In the control samples, the tubes were incubated with saline containing no compound.

The Simultaneous One End Test (SOET) was used to detect the quick blocking effects of the test compounds particularly exerted through sperm motility alterations and is described in Doncel G. F., in "Barrier Contraceptives", Wiley-Liss, Mauck C. K. et al. eds., pp. 147-162 (1994)]. The SOET is similar to the MOET except that the solution containing the test compound was mixed with the semen sample and then one end of the capillary tube containing bovine cervical mucus was inserted into the mixture of the test compound and semen sample and stored in an incubator at 37° C. in an atmosphere of 5% carbon dioxide in air for 60 minutes. Penetration length of vanguard motile sperm was recorded and the results are expressed as percentage of migration as compared to control samples, i.e., saline containing no compound. In the SOET, if not impeded by the test compound, the sperm have the ability to migrate into the tube immediately after contact.

A dose-dependent study showed only minor inhibition of sperm penetration when suramin sodium was tested at 50 mg/mL (5%) in the MOET test. No significant sperm impediment was found at 25 mg/mL or below. At 5%, dextran sulfate showed more inhibition than suramin sodium. For comparison purposes, N-9 completely blocked sperm penetration at 300 µg/mL (0.03%). KY Jelly® (KY), a commercial vaginal lubricant and suramin sodium in KY showed the same degree of inhibition (~40%), which was significantly different from suramin sodium (~4%) alone at the same concentration. No major sperm clumping was observed at any concentration (Table 1).

TABLE 1

Cervical Mucus Blocking Activity of Suramin.

| Compound | Solvent | Dilution | MOET % CTL | n |
|---|---|---|---|---|
| Suramin | 0.9% NaCl | 50 mg/ml | 72.3 ± 7.1 | 10 |
| | | 25 mg/ml | 95.9 ± 1.4 | 10 |
| | | 12.5 mg/ml | 94.9 ± 2.2 | 5 |
| | | 6.25 mg/ml | 96.1 ± 0.9 | 5 |
| Dextran Sulfate | 0.9% NaCl | 50 mg/ml | 56.6 ± 8.9 | 10 |
| | | 25 mg/ml | 86.8 ± 4.4 | 10 |
| | | 12.5 mg/ml | 82.4 ± 5.2 | 5 |
| | | 6.25 mg/ml | 93.7 ± 1.7 | 5 |
| N-9 | 0.9% NaCl | 300 ug/ml | 0.7 ± 0.5 | 10 |
| | | 30 ug/ml | 48.6 ± 6.9 | 10 |
| Suramin-KY | dH2O | 25.5 mg/ml-25% | 64.1 ± 7.6 | 10 |
| KY | 0.9% NaCl | 25% | 61.6 ± 6.9 | 10 |

Viability of Sperm

Viability of sperm was assessed by a sperm membrane integrity evaluation as described in Jeyendran R. S. et al., J. Reprod. Fertil., 70: 219-28 (1984). Aliquots of sperm samples were incubated with suramin or N-9 test compounds. The reaction was terminated by the addition of 1.5 mL Ham's F10. Sperm were centrifuged and the pellet was resuspended in 200 µL of medium. Sperm viability was assessed by placing 100 µL of the sperm suspension in 900 µL of hypo-osmotic swelling test (HOST) medium for 30 min. Coiled sperm tails are a reflection of intact sperm membrane permeability and indicate viable sperm. A minimum of 200 cells were microscopically assessed from each sample.

The results of the sperm membrane integrity evaluation are shown in FIG. 2. No significant differences were observed in sperm viability when suramin-treated samples (10-0.001 mg/mL) were compared to solvent-treated controls. After a fifteen minute co-incubation, motility and viability showed very similar response patterns in both dose and time-dependent experiments, indicating that suramin is not a spermicidal compound.

Human Sperm-Zona Binding

The hemizona assay, as described in Burkman L. J., et al., Fertil. Steril., 49: 688-697 (1988), was used to measure the ability of sperm to undergo capacitation and bind to the zona pellucida of an oocyte. Briefly, in this assay, motile normal sperm were separated in media with bovine serum albumin, which triggers capacitation. Human motile sperm were separated using a swim-up technique and incubated with 1 mM suramin or solvent-control medium for 15 minutes in 100 µL medium droplets covered with mineral oil, at 37° C., 5% $CO_2$. Sperm were then incubated with dead oocytes which are surrounded by the zona pellucida, an acellular coating of oocytes. Bisected hemizonae corresponding to one oocyte were placed each in the test (suramin) and control (solvent) droplets and incubated for an additional 4 hours. Sperm-hemizonae complexes were washed extensively and capacitated spermatozoa bound to the outer surface of the zonae and were counted under an inverted microscope. The Hemizona Index (HZI) was calculated by dividing the number of suramin-treated sperm bound to one hemizona by the number of untreated (control) sperm bound to the other hemizona.

Figure 3:
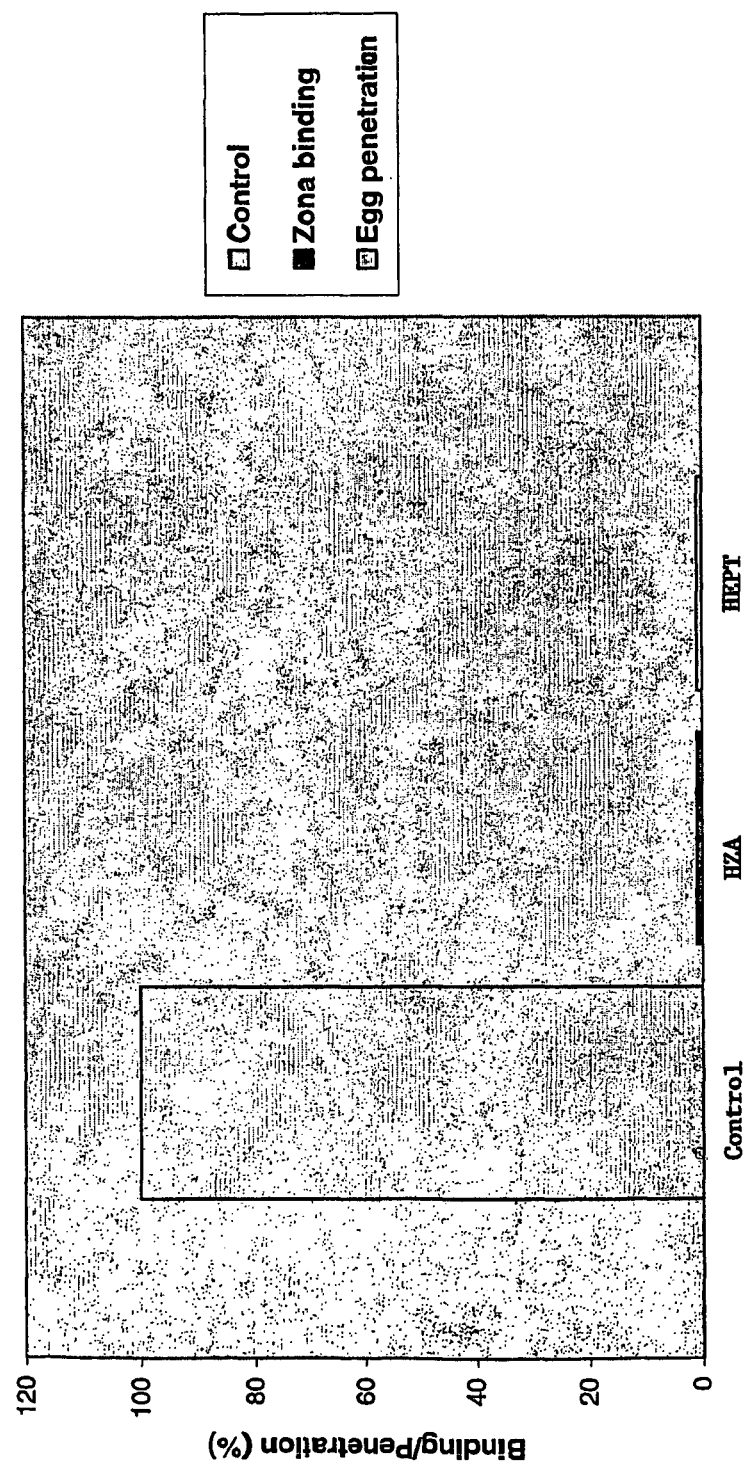
FIG. 3 is a bar graph showing the effect of suramin on human sperm zona binding and hamster egg penetration as more fully described in Example 1. HZA, hemizona assay; HEPT, hamster egg penetration test.

The results of the hemizona assay are shown in FIG. 3. It was found that suramin was a potent sperm-zona binding inhibitor, producing 92% inhibition of human sperm binding at 1 mM (HZI=0.08±0.01, n=9) (FIG. 3). Inhibition may be mediated by blocking zona receptors at the sperm-surface level and/or interfering with signal transduction.

Sperm-Oolemma Binding and Penetration

The hamster-egg penetration test (HEPT) was used to predict the fertilizing ability of human sperm by evaluating the sperm's ooctye-penetration capability as described in Yanagimachi R. et al., Biol. Reprod., 15: 471-6 (1976). The zona pellucida of hamster eggs was dissolved by treatment with a protease, and human sperm were subsequently added to the zona free eggs. Sperm binding and penetration were assessed under a standard microscope (60× magnification) after placing the sperm-egg complexes onto polylysine-coated glass slides and covered them with 22×22 mm glass coverslips. The ability of the sperm to bind and enter the egg was scored by counting the sperm nuclei lying within the egg cytoplasm. The effect of the test compound was determined by comparing the number of sperm bound to the surface of the eggs and the percentage of penetrated eggs.

The results of the HEPT assay using suramin sodium as the test compound are shown in FIG. 3. Suramin sodium showed decreased sperm binding to hamster's zona-free oocytes (~75% inhibition) and completely abolished sperm penetration/fertilization of such eggs in-vitro (n=28 oocytes).

Sperm Hyaluronidase Activity

A hyaluronic acid hydrolysis assay was used to assess the hyaluronidase inhibition properties of suramin sodium. Hyaluronidase is a critical sperm enzyme involved in cumulus penetration. Inhibition of this enzyme renders sperm incapable of transversing the egg vestments, thus impeding sperm-oocyte interaction and, ultimately, fertilization.

Hyaluronidase activity was quantitatively determined by measuring the extent of hyaluronic acid hydrolysis (i.e., the concentration of N-acetylglucosamine-reactive material formed from enzyme activity). Reaction mixtures containing the following were prepared: test compound (variable concentrations of suramin sodium); 0.1 M sodium acetate; 0.15 M sodium chloride; pH adjusted to 5.5; 7.2 units sheep testicular hyaluronidase (Sigma, Type III; H-2251) contained in an acetate buffer; 0.3 mg/ml hyaluronic acid (Sigma, from bovine vitreous humor; H-7630). The enzyme was preincubated with the test agent (1 mg/ml for screening purposes) for 10 minutes before starting the reaction by the addition of hyaluronic acid. The enzyme reaction was determined using the method of Aronson and Davidson (J. Biol. Chem. 241 437-40, 1967). The reaction mixture was incubated for 30 minutes at room temperature. The reaction product is determined calorimetrically with β3-dimethylaminobenzaldehyde (Reissig et al., J. Biol. Chem. 217 959-966, 1965) by measuring the absorbance at 545 nm. Compounds which show no inhibition at the screening concentration of 1 mg/ml are considered to be inactive. If the test agent shows inhibition at the screening concentration, a dose-response curve is generated from which $IC_{50}$ values could be determined using curve-fitting software.

Figure 4:
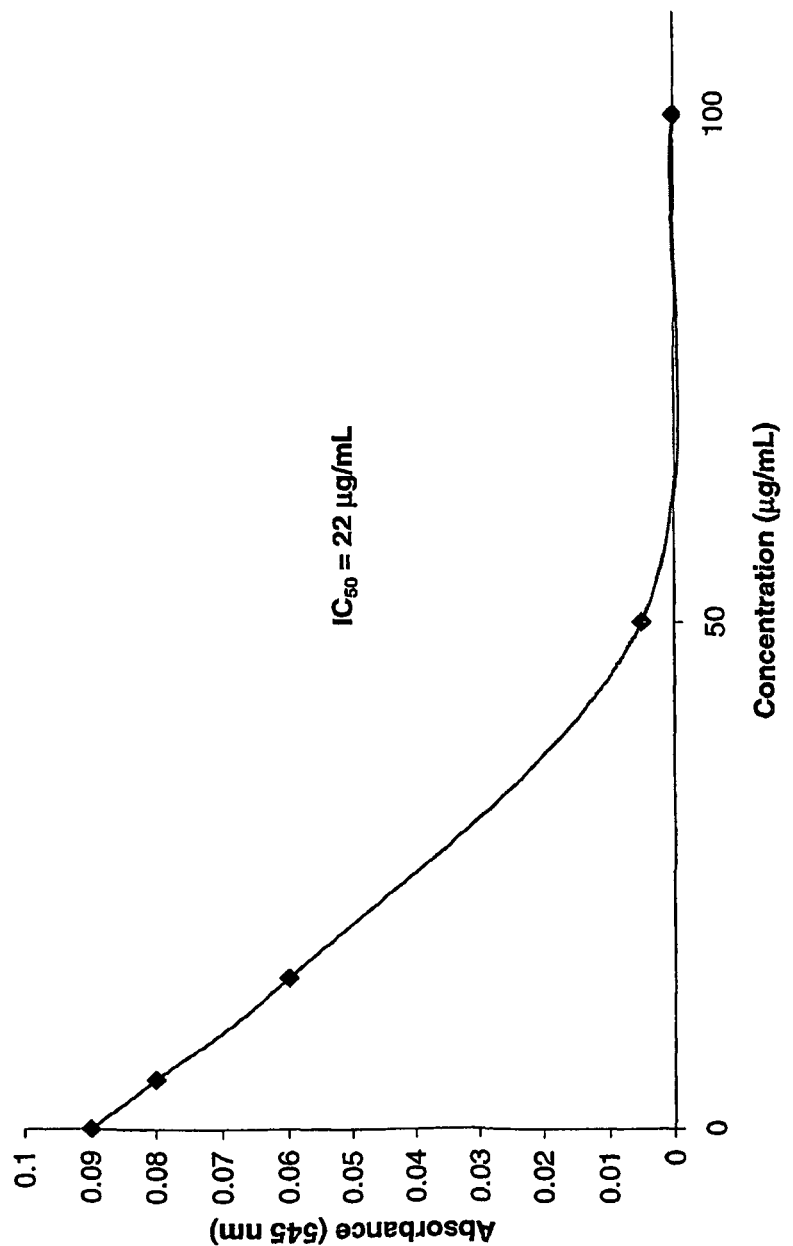
FIG. 4 depicts a graph representing sperm hyaluronidase activity as a function of suramin concentration as more fully described in Example 1.

The results of the Hyaluronidase activity assay tested with suramin sodium are shown in FIG. 4. Suramin sodium proved to be a potent and irreversible inhibitor of hyaluronidase displaying an $IC_{50}$=22 μg/mL. One mg/mL induced 100% inhibition (FIG. 4).

Acrosome Reaction

The acrosome reaction ionophore challenge test (ARIC) was used, as described in Cummins J. M., et al., J. Androl., 12: 98-103 (1991), to measure the proportion of spermatozoa that respond to a calcium ionophore (typically, A23187), developing an acrosome reaction. More specifically, this test was used to determine whether suramin sodium affects the ionophore-induced acrosome reaction of the sperm, therefore altering the capacity of sperm to penetrate an egg. Results are expressed in percent inhibition of control (untreated sperm) acrosome reactions. The results of the ARIC with suramin sodium are shown in Table. 2.

TABLE 2

Effect of Suramin on Human Sperm Acrosome Reaction

| Compound | Calcium-ionophore treatment (5 μM A23187) | Percentage of acrosome-reacted Sperm | n |
|---|---|---|---|
| Suramin Sodium | − | 5.28 ± 1.93 | 6 |
| Control | − | 5.39 ± 1.38 | 6 |
| Suramin Sodium | + | 31.4 ± 15.1 | 6 |
| Control | + | 29.8 ± 13.0 | 6 |

Referring to Table 2, suramin sodium appeared neither to stimulate spontaneous acrosome reaction (acrosomal loss) nor to block the $Ca^{2+}$ ionophore-induced reaction, as has been described for other sulfated and sulfonated compounds, especially polymers.

Rabbit Contraceptive Efficacy Trials

Semen was collected from New Zealand White (NZW) male rabbits with the aid of an artifical vagina, pooled and adjusted with a modified Tyrode's albumin lactate pyruvate (TALP) medium to 50 million motile sperm per milliliter. Ovulation was induced in females by injection of 200 IU of human chorionic gonadotropin (hCG) intravenously. Under the ex-vivo (in-vitro) mixing protocol, sperm were incubated with indicated suramin test compounds in a tube for 15 minutes at 37° C. prior to insemination (0.5 mL) as described in Anderson R. A., et al. J. Androl., 21: 862-875 (2000). If the suramin composition showed contraceptive activity following this protocol, it was then tested in a formulation which is applied intravaginally (1 mL) 15-30 minutes before insemination. Sperm-compound contact, in this case, took place in vivo, inside the vagina. Insemination and administration of the compound was performed with a flexible, 12 cm long polyurethane catheter. The main endpoints for both protocols were the number of implantation sites counted 11 days after insemination and pregnancy rate. Such sites were counted by visual inspection of the tubes.

Ex Vivo Trial

Referring to Table 3, under an "ex-vivo mixing" format where sperm were incubated in-vitro with medium with or w/o suramin sodium, 1 mM (1.4 mg/mL) concentrations inhibited pregnancy rates (PR) by 86% (1/7) also reducing the number of implantation sites (IS) from 6.4±0.9 in controls to 1 in the test group. A concentration of 0.1 mg/mL did not significantly reduce PR, although it slightly decreased IS from 7.7±1.2 to 4.4±0.8. A five percent (5%) concentration completely prevented pregnancies (0/7). The results are shown in Table 3.

TABLE 3

Contraceptive efficacy of suramin sodium after ex-vivo sperm mixing

| Compounds | Suramin Concentration (mg/ml) | Number of Pregnant Females/Total | Pregnancy Rate (%) | Implantation Sites (Mean ± SD) |
|---|---|---|---|---|
| Medium control | 0 | 7/7 | 100 | 7.7 ± 1.2 |
| Suramin | 0.1 | 5/6 | 83 | 4.4 ± 0.8 |
| | 1.4 | 1/7 | 14 | 1 |
| | 50 | 0/7 | 0 | N.A. |

Pooled rabbit sperm were mixed with suramin at various concentrations, in vitro, for 15 minutes, before insemination. Females were induced to ovulate with hCG and then intravaginally inseminated with 50 million, treated or untreated motile sperm/mL (0.5 mL). Pregnancy and implantation sites were evaluated 11 days post-insemination.

In Vivo Trial

After intravaginal administration of 5% suramin sodium in KY Jelly® (KY) or carboxymethyl cellulose (CMC) followed by artificial insemination, there was a 75% reduction in PR (2/8). In order to verify a potential additive effect which could increase suramin's efficacy, a pilot study was performed adding a mild non-ionic surfactant, sorbitan monolaurate, to the suramin sodium/KY formulation. PR for control, 2% sorbitan, 2% suramin sodium, and 2% sorbitan+2% suramin sodium were 100%, 100%, 44%, and 0%, respectively (Table 4). Another experiment combining 5% suramin with 0.1% N-9 in KY also showed synergistic effects.

TABLE 4

Contraceptive Efficacy of Suramin Sodium After Intravaginal Application and Cooperative Effects of Surfactants

| Compounds | Concentrations of Actives (mg/mL) | Number of Pregnant Females/ Total | Pregnancy Rate (%) | Implantation Sites (Mean ± SD) |
|---|---|---|---|---|
| KY Jelly ® | 0 | 7/8 | 87.5 | 5.9 ± 0.8 |
| Suramin in KY | 50 | 2/8 | 25 | 8.5 ± 0.5 |
| Suramin in KY | 20 | 4/9 | 44 | 5.0 ± 1.1 |
| Sorbiton ML in KY | 20 | 4/4 | 100 | 3.0 ± 1.0 |
| Suramin + Sorbitan ML in KY | 20 + 20 | 0/4 | 0 | N.A. |

Control and test formulations were administered intravaginally (1 mL) to females before induction of ovulation with hcG. Fifteen to thirty minutes later, the females were inseminated with normal untreated pooled rabbit sperm (50 million motile sperm per milliliter 0.5 mL)

Referring to Table 5, a synergistic effect was clearly evident when suramin was formulated at various concentrations, from 5% to 1.25%, in a carbopol-based vaginal lubricant gel, Replens®. Even the lowest dose studied, 1.25%, was 100% contraceptive (PR=0%). The PR in the control group (Replens® alone) was 100%.

TABLE 5

Contraceptive Efficacy of Suramin Formulations - Dose Response

| Compounds | Suramin Concentration (mg/mL) | Number of Pregnant Females/ Total | Pregnancy Rate (%) | Implantation Sites (Mean ± SD) |
|---|---|---|---|---|
| Replens ® (control) | 0 | 4/4 | 100 | 10.5 ± 1.73 |
| 5% suramin in Replens ® | 50 | 0/4 | 0 | N.A. |
| 2.5% suramin in Replens ® | 25 | 0/4 | 0 | N.A. |
| 1.25% suramin in Replens ® | 12.5 | 0/4 | 0 | N.A. |

Female rabbits were administered intravaginally with 0.75 mL of compound and 15-30 minutes later inseminated with pooled rabbit sperm. Implantation sites were visualized 11 days after insemination A summary of the anti-sperm and contraceptive activity of the compounds of the present invention is provided in Table 6.

TABLE 6

Summary of anti-sperm and contraceptive activity of suramin compositions

| Type of Activity | Inhibition/ Inactivation | Assays | Potency | Comments |
|---|---|---|---|---|
| Anti-Sperm (in-vitro) | Motility | Sander Cramer Motility CASA | None | Highest concentration = 25 mg/mL Time and dose-dependent exps. Computer-assisted motion analysis |
| | Viability | HOST | None | Time- and dose-dependent exp. |
| | CM Penetration | MOET SOET | Very low | Tested formulated (5%) and unformulated |
| | ZP binding | HZA | High | 92% inhibition at 1 mM-Reversible |
| | Oolemma binding/ Penetration | HEPT | High | 75% and 100% inhibition of binding and penetration, respectively |
| | Hyaluronidase | Hyaluronic Acid Hydrolysis | High | $IC_{50}$ = 22 µg/mL-Irreversible |
| | Acrosome Reaction | ARIC | None | Induction or inhibition of acrosome reaction |
| Contraception (in-vivo) | Rabbit pretreated sperm | In-vitro mixing | Moderate | 100% inhibition at 5% in KY Jelly ®; 86% inhibition at 0.1% (~1 mM) |

TABLE 6-continued

Summary of anti-sperm and contraceptive activity of suramin compositions

| Type of Activity | Inhibition/ Inactivation | Assays | Potency | Comments |
|---|---|---|---|---|
| | Rabbit inseminated sperm | Vaginal Application | Moderate | 75% inhibition at 5%; 44% at 2% |
| | | Vaginal Application Combo | High | 100% inhibition at 2% suramin + 2% sorbitan mono laurate or 0.1% N-9 |
| | | Vaginal Application | High | 100% inhibition at 1.25% Replens ® |

Example 2

Anti-Microbial Activity

Activity Against HIV

Inhibition of HIV Infectivity: Virus Binding Inhibition Assay

VBIAIIIB: MT-2 cells, compounds and virus (HIV-1 IIIB) were mixed together in 96-well plates and incubated for 2 h at 37° C. At the end of this incubation period, the 96-well plates were centrifuged for 10 minutes and approximately 175 µL of medium was removed using a multichannel pipettor and replaced with 175 µL of fresh media. Cultures were then incubated at 37° C. for 6 days. Modulation of virus induced cytopathic effects was measured by determining percent reduction in optical density (O.D.) using an XTT (2,3-bis(2-methoxy-4-nitro-5-sulfophenyl)-5-[phenylamino)carbonyl]-2H-tetrazolium hydroxide) dye reduction assay. Virus-induced cytopathic effects and mechanical artifacts due to media removal were verified by microscopic observations (Anderson R. A., et al., J. Androl., 21: 862-875 (2000)). The results of this assay are provided herein.

C-MAGI/Ba-L Assay

The C-MAGI/Ba-L assays were carried out with MAGI-CCR-5 cells. The cell line was maintained in DMEM medium containing 10% FBS, 100 U/ml penicillin, 300 µg/mL glutamate and selection antibiotics as indicated above. Before assay, the cells were placed in 96 well flat tissue culture plates at $1 \times 10^4$ cells per well, and incubated overnight in the absence of antibiotics. The next day, medium was removed, and virus and compound (100 µL virus ($HIV_{Ba-L}$)+100 µL compound) were added. The cultures were incubated for 2 hours to facilitate virus attachment. After this incubation, the medium is removed from the wells, replaced with fresh compound-free medium, washed twice and finally incubated at 37° C. for 2 days in fresh medium. Following incubation, the medium was removed and induction of β-galactosidase enzyme activity was detected by chemiluminescence. β-galactosidase activity was detected using a chemiluminescence substrate, following the manufacture's instructions (Tropix). The $TC_{50}$ and $IC_{50}$ are determined using linear regression and a therapeutic index or antiviral index calculated. The results of this assay are provided herein.

ME-180-Based Topical Microbicide Assay

ME-180 cervical epithelial cells were plated in the interior wells of a 96-well flat bottom microtiter plate at a density of $5 \times 10^3$ cells per well and incubated overnight. Chronically infected H9 cells (H9-SK1) were treated with 200 µg/ml mitomycin C (Sigma) in complete medium for one hour, washed extensively and resuspended at $4 \times 10^5$ per ml. The concentration of mitomycin C used resulted in the killing of the chronically infected cells within 48 hours treatment, allowing sufficient time for cell-cell transmission of virus to the ME-180 cells while assuring that the virus endpoint quantification would not include a contribution from the chronically infected cells. Antiviral compounds and chronically infected cells ($2 \times 10^4$ cells) were added to each well containing ME-180 cells and incubated for 6 hours. Following co-cultivation, the monolayer was washed extensively and fresh medium was added. Medium was removed and fresh medium was added at 24 and 48 hours post-infection to remove dead lymphocytes. On day 6 post-infection, supernatant samples were removed and analyzed for virus content by p24 ELISA (Phillips D M et al., 1995, J Virol Methods, March, 52 (1-2): 1-13). The results of this assay are provided below.

Cell-to-Cell Transmission (CTC) Assay

HIV-1-infected SupT1 cells (strain IIIB), killed by prior exposure to mitomycin C (200 µg/mL) for 1 hour at 37° C., were incubated with each agent and P4-R5 (MAGI) cells for 2 hours at 37° C. Following the incubation period, cells were washed and provided with new media. Successful transmission and subsequent replication events were quantitated using Galacto-Star assay 48 hr post-infection. Infected cells were expressed as a percent of cells infected after mock exposure. In each assay, triplicate wells were tested for each concentration. The results of this assay are provided herein.

Clinical Isolates in Peripheral Blood Mononuclear Cells (PBMCs): PBMC Isolation and Blasting Peripheral blood mononuclear cells (PBMCs) were obtained from normal hepatitis and HIV-1 negative donors by ficoll hypaque gradient separation. Briefly, anti-coagulated blood is diluted 1:1 with Dulbecco's phosphate buffered saline without $Ca^{++}$ and $Mg^{++}$ (PBS) and layered over 14 mL of Lymphocyte separation media in a 50 ml centrifuge tube. Tubes were then centrifuged for 30 minutes at 600×g. Banded PBMCs were gently aspirated from the resulting interface and subsequently washed 2× with PBS by low speed centrifugation. The mononuclear cells were counted, viability was determined by Trypan Blue dye exclusion and the cells were resuspended in RPMI 1640 medium supplemented with 15% FBS (heat inactivated), 2 mM L-glutamine, 100 U/mL penicillin, 100 µg/mL streptomycin, and 10 µg/mL gentamycin with 20 U/mL recombinant IL-2 (R&D Systems, Minneapolis, Minn.). IL-2 was included in the culture medium to maintain the cell division initiated by PHA mitogenic stimulation. The cultures were then maintained until use by ½ culture volume change with fresh IL-2 containing medium every 3 days. Most assays were initiated with 3-day old blasted PBMCs. The results of this assay are provided herein.

PBMC Assay

Human peripheral blood mononuclear cells from a minimum of two donors, that have been stimulated with PHS- and IL-2, were counted and their viability was determined by Trypan Blue dye exclusion and mixed in equal rations. Pooled donors were used to minimize the variability observed between individual donors, which results from quantitative and qualitative differences in HIV infection, and overall response to the PHA and IL-2 of primary lymphocyte populations. The cells were resuspended at $1\times10^6$ cells/mL in RPMI 1640 without phenol red supplemented with 15% Fetal Bovine Serum (heat inactivated), 2 mM L-glutamine, 100 U/mL penicillin, 100 µg/mL streptomycin, 10 µg/mL gentamycin and IL-2 (20 U/mL, R&D Systems, Minneapolis, Minn.). Fifty microliters of cells were then distributed to the inner 60 wells of a 96 well round bottom microtiter culture plate in a standard format. Each plate contained cell control wells (cells only), virus control wells (cells plus virus), and experimental wells (drug plus cells plus virus). Serially diluted compounds were added to the microtiter plate followed by the appropriate pre-titered strain of HIV-1. The plates were then incubated for 6 hours at 37° C., 5% $CO_2$, centrifuged at approximately 300×g for 10 minutes and 175 µL of supernatant removed with a multi-channel pipetor and replaced with fresh compound-free media. The final volume per well was 200 µL. All samples were assayed in triplicate with a replicate plate without virus for the determination of compound toxicity. The assay was incubated for 6 days in a humidified atmosphere at 37° C., 5% $CO_2$, after which supernatants were collected, for analysis of RT activity and sister plates analyzed for cell viability by XTT dye reduction. Wells were also examined microscopically and any abnormalities were noted. The results of this assay are provided herein.

XTT Staining for Cell Viability and Compound Cytotoxicity $TC_{50}$ values for the test materials were derived by measuring the reduction of the tetrazolium dye XTT (2,3-bis(2-methoxy-4-nitro-5-sulfophenyl)-5-[(phenylamino)carbonyl]-2H-tetrazolium hydroxide) in replicate microtiter plates containing cell and compound without virus. XTT in metabolically active cells was metabolized by the mitochondrial enzyme NADPH oxidase to a soluble formazan product. XTT solution was prepared daily as a stock of 1 mg/mL in PBS. Phenzaine methosulfate (PMS) solution was prepared at 15 mg/mL in PBS and stored in the dark at −20° C. XTT/PMS stock was prepared immediately before use of diluting the PMS 1:100 into PBS and adding 40 µL per mL of XTT solution. Fifty microliters of XTT/PMS are added to each well of the plate and the plate incubated for 4 hour at 37° C. The 4 hour incubation was empirically determined to be within the linear response range for MTS dye reduction with the indicated numbers of cells for each assay. Adhesive plate sealers were used in place of the lids, the sealed plates were inverted several times to mix the soluble formazan product and the plates were read at 450 nm with a Molecular Devices SpectraMax Plus 96 well plate format spectrophotometer. The results of this assay are provided herein.

Reverse Transcriptase Assay

Reverse transcriptase activity, a measurement of virus replication, was measured in cell-free supernatants. Tritiated thymidine triphosphate (NEN) (TFP) was resuspended in distilled $H_2O$ at 5 Ci/mL. Poly rA and oligo dT were prepared as a stock solution which was kept at −20° C. The RT reaction buffer was prepared fresh on a daily basis and consisted of 125 µL 1.0 M EGTA, 125 µL $dH_2O$, 110 µL 10% SDS, 50 µL 1.0 M Tris (pH 7.4), 50 µL 1.0 M DTT, and 40 µL 1.0 M $MgCl_2$. These three solutions were mixed together in a ratio of 2 parts TTP, 1 part poly rA:oligo dT, and 1 part reaction buffer. Ten microliters (10 µL) of this reaction mixture was placed in a round bottom microtiter plate and 15 µL of virus containing supernatant added and mixed. The plate was incubated at 37° C. for 60 minutes. Following reaction, the reaction volume was spotted onto pieces of DE81 paper, washed 5 times for 5 minutes each in a 5% sodium phosphate buffer, 2 times for 1 minute each in distilled water, 2 times for 1 minute each in 70% ethanol, and then dried. Opti-Fluor 0 was added to each sample and incorporated radioactivity quantitated utilizing a Wallac 1450 Microbetaplus liquid scintillation counter. The results of this assay are provided herein.

Infection of T Cells by HIV Associated to Dendritic Cells (DC/T Assay)

Monocyte-derived dendritic cells (MO-DC), infected with the NSI/R5 strain Ba-L at 10-3 multiplicity of infection, were cultured alone or with autologous CD4(+) T cells at a ratio 1:1 or 1:10. A dilution series of suramin was added to the MO-DC, 1 hour prior to infection and remained present during infection. After infection, cells were extensively washed and compounds were added at the same concentrations as for the pre-incubation. Medium and compounds were refreshed twice a week. After 2 weeks, HIV Ag was measured in supernatants with ELISA and $EC_{50}$ values (effective conc. 50%) were calculated using linear regression (Vanham G et al, AIDS 2000, 14: 2299-2311). The results of this assay are provided herein.

Results

Suramin has previously been reported to confer protection to T cells in vitro against the infectivity, replication and cytopathicity caused by human T-cell lympotropic virus (HTLV-M) (Mitsuya H et al. Science, October; 226(4671): 172-4, 1984; Balzarini J. et al. Int. J. Cancer., 37: 451-7, 1986). Furthermore, it was tested in patients with Kaposi's Sarcoma or AIDS-related complex with a partially successful outcome (Broder S. et al., Lancet., 2(5456):627-30, 1985). However, suramin was never evaluated or intended for use as an intravaginal or intrarectal method to prevent sexual transmission of HIV. Systemic toxicity and a poor therapeutic index were the main reasons not to continue with clinical trials. These reasons, as well as suramin's long half life and high protein binding, precluded others from identifying a topical application of suramin to prevent sexual transmission.

Figure 5:
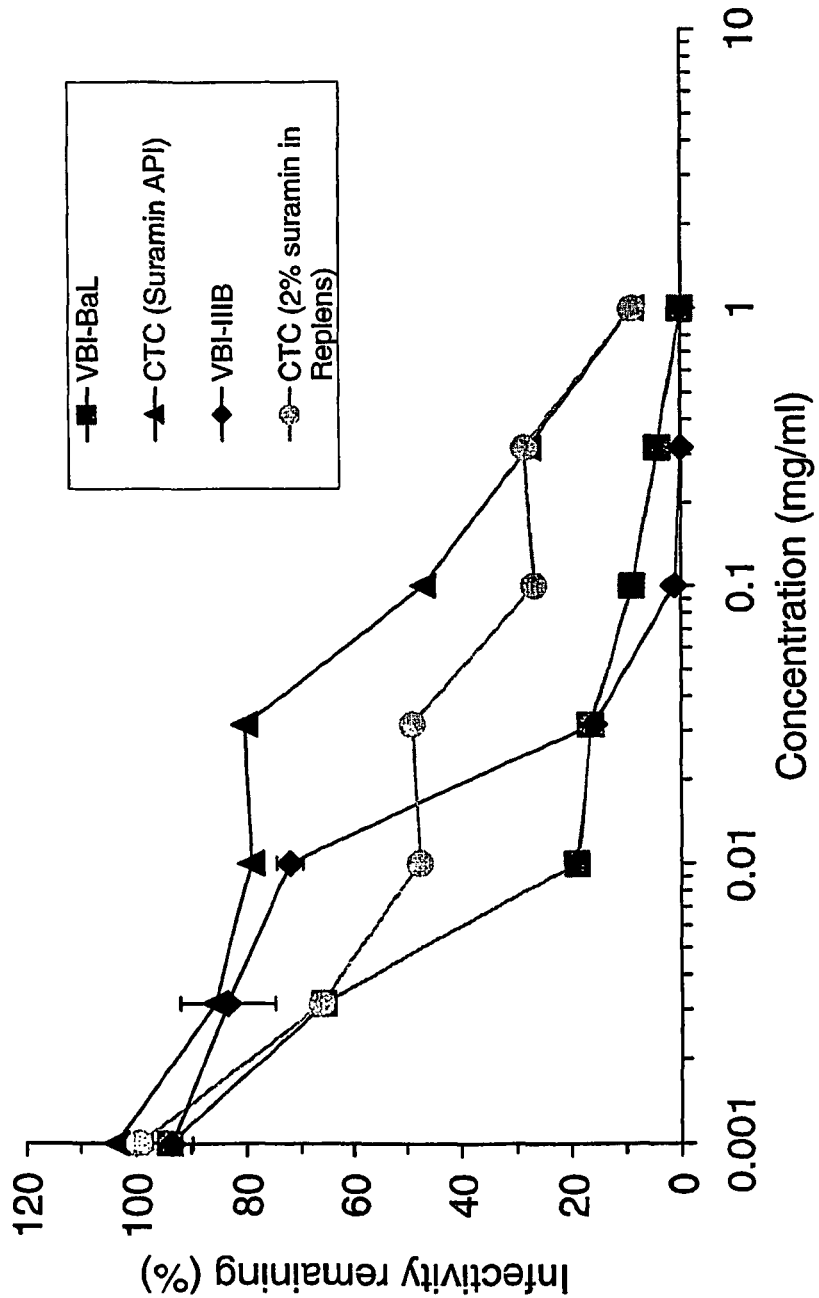
FIG. 5 depicts the infectivity remaining in indicated cells as a function of pre-determined suramin concentrations as more fully described in Example 2. VBI-BaL, viral entry inhibition assay with the monocytotropic HIV-1 strain BaL; CTC, cell-to-cell transmission assay; VBI-IIIB, viral entry inhibition assay with the lymphocytotropic HIV-1 strain IIIB; API, active pharmaceutical ingredient (suramin drug substance).

Suramin sodium was found herein to be highly active against lympho- and monocytotropic strains of HIV-1 ($IC_{50}$=7.3 µg/mL [72 hours incubation] and 18.5 µg/mL [2 h-incubation] against IIIB in viral entry assays and 0.34 and 5.5 µg/mL against Bal [2h-incubation]) (FIG. 5). It was also effective in a CD4-independent epithelial cell transmission assay (ME-180 assay; $IC_{50}$=24.5 µg/ml.) (FIG. 6), a CD4-dependent cell-to-cell transmission assay (CTC assay; $IC_{50}$=93.5 µg/mL) (FIG. 5) and in the dendritic cell (DC)/T lymphocyte model ($IC_{50}$=17 µg/mL) (results shown in Table 7).

TABLE 7

Inhibition of HIV Transmission from Dendritic Cells to T Cells

| Compound | Cells Effecting Transmission | | |
|---|---|---|---|
| | Dendritic Cells (DC) | DC + T Cells (1:1) | DC + T Cells (1:10) |
| Suramin ($EC_{50}$ in µg/mL) | 56 ± 6 | 57.5 ± 5 | 17 ± 3 |

DC infected with BaL (R5 HIV-1) were cultured alone or in combination with autologous T lympocytes at two ratios in the presence of multiple concentrations of suramin.

Figure 6:
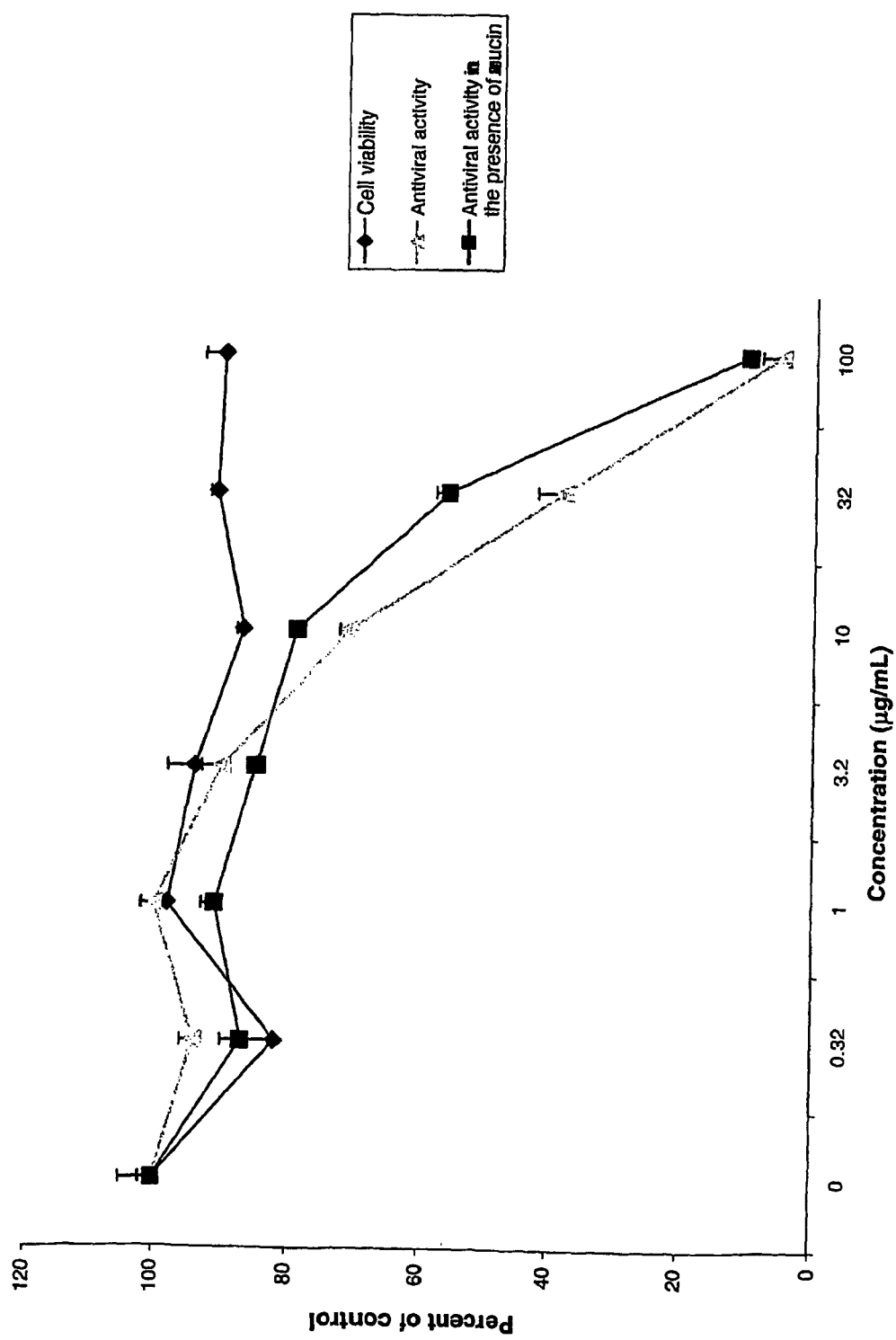
FIG. 6 is a graph depicting inhibition of epithelial cell transmission of HIV-1 by suramin in the presence and absence of mucin as more fully described in Example 2.

Addition of mucin in the ME-180 assay to resemble cervicovaginal secretions did not significantly reduce suramin's activity (FIG. 6). Formulating suramin at 2% in KY Jelly® maintained its antiviral activity intact. Interestingly, formulating suramin in Replens®, a carbopol-based vaginal lubricant, had a significant synergistic effect, especially in suramin's antiviral activity against cell-free and cell-associated HIV-1 IIIB (Table 8).

TABLE 8

Anti-HIV Activity of Suramin Formulations

| Compound | Cell-Free Strains | | Cell-Associated Strains |
|---|---|---|---|
| | IIIB (mg/mL) | BaL (mg/mL) | IIIB (mg/mL) |
| Suramin | 18.5 | 5.5 | 93.5 |
| 2% suramin in KY Jelly ® | 24.4 | 3.16 | 287.5 |
| 2% suramin in Replens ® | 2.1 | 7.2 | 9.6 |
| Positive control | 1.6 | 14.6 | 12.9 |

Data represent 50% inhibitory concentrations ($IC_{50}$) Target cells are CD4/coreceptor expressing HeLa cells. Incubation time: 2 hours The preventative aspects of the compositions and methods of the invention have not been fully appreciated prior to the instant invention. For example, prior to the present invention, it was known that HIV infects the vaginal mucosa in less than 2 hours after contact (Hu J et al., J Virol 2000 July; 74(13): 6087-95), and the rectal mucosa likely in a shorter time. However, all the reported assays purporting to describe suramin anti-HIV activity used prolonged incubations (days), wherein the compound was present during the entire incubation period. While appropriate for a therapeutic application, this mode of evaluate is inappropriate for a method of describing the prevention of vaginal or rectal transmission of HIV, where the agent should act during a window of infectivity that starts at the time of sexual contact and ends as soon as the compound falls below effective concentrations (e.g., due to leakage and dilution) or the virus is inactivated by the renewed acidic vaginal pH.

Moreover, epithelial cells and dendritic cells, present in vaginal and rectal mucosa, are capable of being infected or transmit live virus even after several days after the initial infection. It has now been discovered that suramin is capable of blocking CD4-independent epithelial and dendritic cell infection, two events without which prevention of sexual transmission would not be possible.

In order to prevent mucosal transmission of HIV, including cervical-vaginal HIV infections as described herein, a variety of key experimental data regarding the function and effectiveness of the compositions should be obtained. For example, the compound or composition should a) inactivate the virus or inhibit HIV entry within less than 2 hours of contact with the virus, for that is the accepted time frame in which the virus infects the vaginal mucosa; b) be effective against cell-associated virus, which is a critical component of the HIV load in semen (i.e., block cell-to-cell transmission); c) block infection of epithelial cells, as well as CD-4-bearing cells; d) block HIV infection of and transmission by dendritic cells (one of the primary targets in mucosal transmission); and e) inhibit monocytotropic HIV-1 strains (predominant in sexual transmission).

It has been demonstrated herein that suramin possesses all the above-mentioned characteristics. Furthermore, it has also been shown herein that suramin is not toxic to the vaginal epithelium or lactobacilli, hydrogen peroxide producing bacteria that control the growth of pathogenic microorganisms, and displays anti-inflammatory activity on vaginal cells (i.e., inhibits vaginal secretion of proinflammatory cytokines). This latter finding makes suramin an ideal agent to combine with surfactants, virus inactivators, antimicrobials, and microbicides which, because of their nature, display proinflammatory activity, a feature that favors HIV mucosal transmission. Moreover, it has not been demonstrated that suramin, when administered vaginally, exhibits negligible bioavailablity.

If a compound does not have the above-mentioned characteristics, one skilled in the art would recognize that the compound or composition can not be recommended as a prophylactic for sexual transmission of HIV.

Activity Against HSV

Evaluation of anti-HSV activity of suramin was based on the method described by Herold et al., J. Virol., 70: 3461-3469 (1996). The compound was serially diluted (1000 µg/ml to 1.0 µg/ml) in phosphate-buffered saline (PBS), and each dilution was mixed with each of two serial dilutions ($10^{-5}$ and $10^{-6}$) HSV (type 2 strain 333). Working viral titers were approximately $10^3$ and $10^4$ plaque forming units (pfu) per ml, respectively. Samples (1 ml) of each mixture were plated in duplicate on washed and drained confluent monolayers of CaSki cells (a human cervical epithelial cell line, obtained from the American Type Culture Collection, Rockville, Md.) on the bottoms of 25 cm² flasks. Initial titer (indicated in the control cultures with no added test agent) in each culture was given as pfu/ml. The flasks were incubated for 2 hours, after which the medium (containing virus and test compound) was removed and the cells were washed with PBS. Cells were cultured for 3 days in medium 199, supplemented with 1% serum and 0.5% methyl cellulose that contained anti-HSV antibodies to prevent the formation of secondary plaques. Cells were stained with Giemsa for the counting of viral plaques by phase contrast microscopy. The viral titer was inferred from the number of plaques, after correction for dilutions. Values were corrected to a control titer 5×10⁸ pfu/ml. Data were expressed as viral titer and as the percentage of plaques that are counted in control cell cultures (not exposed to test agent). Test compounds that showed no activity at 100 µg/ml were considered inactive as anti-HSV agents. The concentration of the compound that was required to reduce the viral titer by 50% ($IC_{50}$) was estimated with curve-fitting software (TableCurve 2D, version 3.02) from plots of plaque-forming units (pfu) per ml as a function of concentration of the compound.

Figure 7:
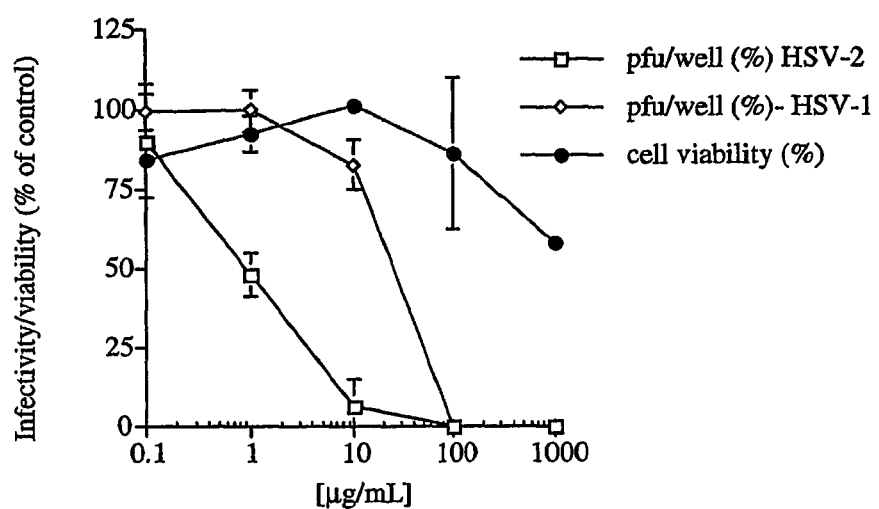
FIG. 7 is a graph showing the anti-herpes activity and cytotoxicity of suramin as more fully described in Example 2.

Suramin sodium was highly effective against HSV-2 as well, exhibiting 100% inhibition of viral infectivity at 100 µg/mL in a plaque assay. Results are shown in FIG. 7. While not being significantly cytotoxic at the highest concentration tested (1000 µg/mL), suramin's $IC_{50}$ against HSV-2 and HSV-1 were 1 and 30 µg/mL, respectively.

Activity Against Cytomegalovirus

In a cytomegalovirus binding assay, tritiated murine cytomegalovirus (MCMV) was incubated with NIH3T3 fibroblasts in a 24-well plate fixed (0.4% paraformaldehyde) for 2 hours at 37° C. (rocking) in the presence of media alone or media containing 1-1000 µg/mL suramin. Cells were then washed extensively and lysed with 1% SDS and triton X-100. Lysates were quantified for radioactivity (cpm) in a scintillation counter.

Figure 8:
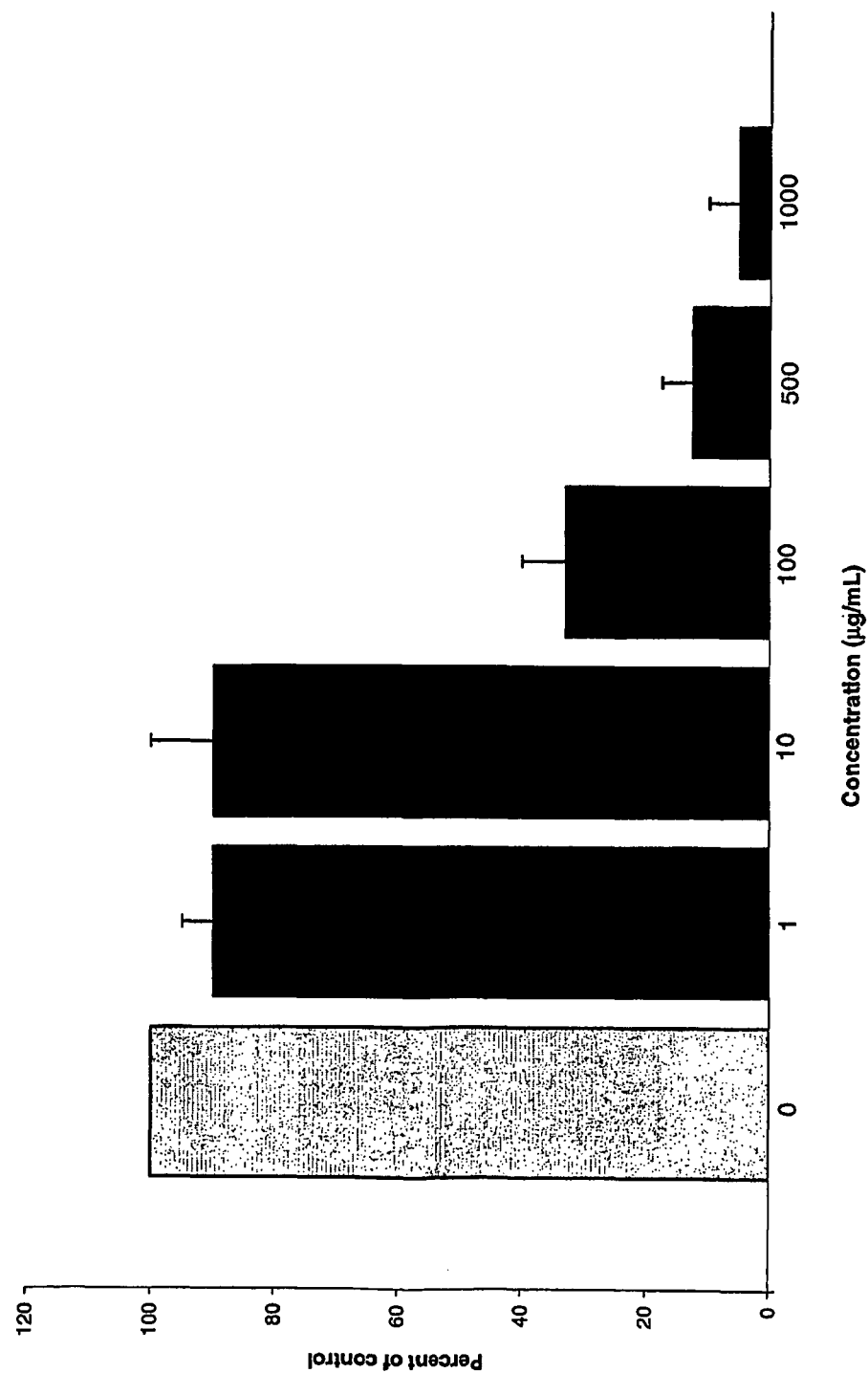
FIG. 8 depicts a bar graph representing inhibition of cytomegalovirus binding to fibroblasts as a function of the concentration of suramin as more fully described in Example 2.

Suramin sodium was also effective against CMV, displaying an $IC_{50}$=50 µg/mL in a binding assay, as seen in FIG. 8.

Activity Against *Chlamydia trachomatis* (CT)

*Chlamydia* multiplication inhibition was performed according to Cooper M. D. et al., J. Gen. Microbiol., 136: 1109-1115 (1990). Prior to experimentation, cryo-preserved *Chlamydia trachomatis* (serotype E/UW-5/CX) were quickly thawed (37° C.) and suspended by mild sonication. Serial 1:10 dilutions of the bacterial suspension were made, ranging from $10^{-1}$ to $10^{-7}$.

HeLa monolayers (on coverslips) were inoculated with 100 µl of the different dilutions of chlamydia (elementary bodies), in the presence or absence of test agent. The suramin compound was tested at 0.1, 1.0, 10, 100 and 1000 µg/ml. After 1 hour, the monolayers were washed to remove free chlamydia and test agent, and they were incubated for 48 hours.

Medium was removed, and the HeLa monolayers were fixed in methanol, washed, and treated with Kallsted *Chlamydia* Culture Confirmation fluorescein-conjugated Monoclonal Antibody. Reaction of labeled antibody with the cells was carried out for 30 minutes at room temperature (i.e., 25° C.) (no light) in a humidified chamber. The cells were washed with water; a drop of mounting medium is placed on a glass slide, and the coverslip was applied. Inclusions due to chlamydial infection were visualized with a fluorescent microscope as green fluorescence. Data was reported as the number of inclusion forming units per ml of undiluted chlamydial titer, and were adjusted to control values of 2.6× $10^7$ IFU/ml for control cultures (no test agent) in each experiment. Compounds that show no activity at 1000 µg/ml are considered to be inactive as anti-chlamydial agents. After logarithmic transformation of all data, dose-response curves were created with curve-fitting (TableCurve 2D, version 3.02; Jandel Scientific) software.

Figure 9:
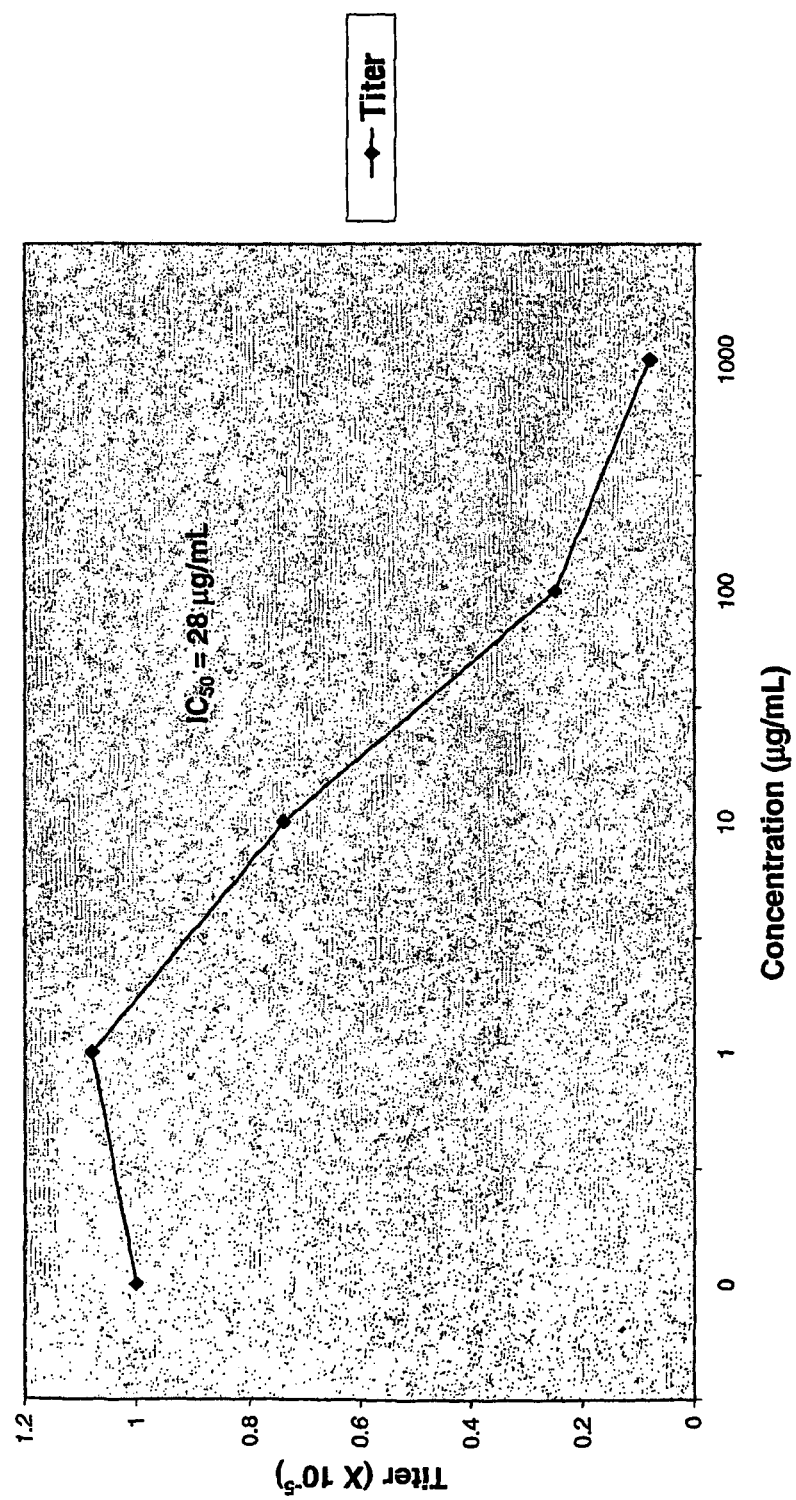
FIG. 9 depicts a graph showing the titer of *Chlamydia trachomatis* after treatment with various concentrations of suramin as more fully described in Example 2.

Suramin sodium inhibited CT multiplication by 75% at 100 µg/mL ($IC_{50}$=28 µl/mL) (FIG. 9). At 2 mg/mL, inhibition was essentially complete (control titer: $1\times10^{-5}$, suramin sodium titer: $0.08\times10^{-5}$).

*Neisseria gonorrhoeae* (GC)

Gonococcal Growth Inhibition

Gonococcal growth inhibition assays were performed by the method of Anderson R. A., et al., J. Androl., 21: 862-875; 2000. Briefly, *Neisseria gonorrhea* from local uncomplicated cases of gonorrhea were isolated (verified by Gram stain, oxidase reactivity and sugar fermentation). The titer of log-phase cultures were adjusted by dilution in GC broth to 0.5 McFarland standard (approximately $10^8$ colony forming units per ml). This was diluted 1:10 with broth that contained no additions (control), and each of serial 1:10 dilutions of test agent, ranging from 1 mg/ml to 1.0 µg/ml. The cultures were incubated at 37° C. for four hours. Four serial 1:10 dilutions were made in GC broth, and a portion of each dilution was inoculated onto GC agar plates. The plates were incubated overnight, and resultant gonococcal colonies were counted under bright-field microscopy. Data for each concentration of suramin were expressed as the number of colony-forming units (CFU) per ml of the original log-phase bacterial suspension.

Figure 10:
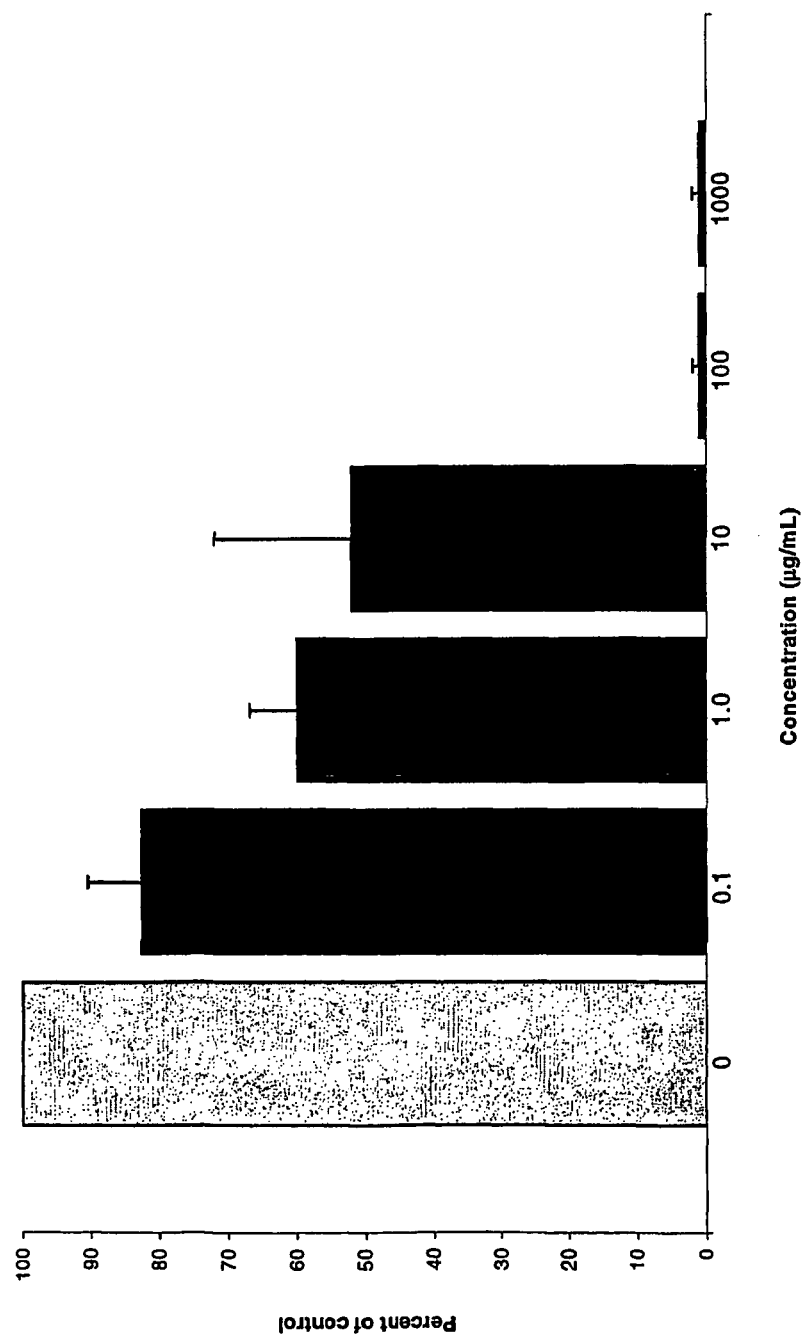
FIG. 10 is a bar graph depicting growth of *Neisseria gonorrhoeae* as a function of indicated concentrations of suramin determined by the *N. gonorrhoeae* (MSIIA) multiplication (growth) assay as more fully described in Example 2.

Referring to FIG. 10 (testing of suramin tested at 1-1000 µg/mL), there was no clear dose-response. However, suramin sodium completely inhibited GC growth (multiplication assay) at 1 mg/mL.

A summary of the antimicrobial activity of the suramin compositions of the present invention is provided in Table 9.

TABLE 9

Summary of antimicrobial activity of suramin compositions.

| Type of Activity | Inhibition/ Inactivation | Assays | Potency | Comments |
| --- | --- | --- | --- | --- |
| Anti- Microbial (in vitro) | HIV-1 | VBIA-IIIb | High | $IC_{50}$ = 7.3 µg/mL |
| | | MAGI-Bal | High | $IC_{50}$ = 0.39 µg/mL |
| | | ME-180 | High | $IC_{50}$ = 24.5 µg/mL |
| | | Clin Isolates | High | $IC_{50}$ = 14.6 µg/mL |
| | | CTC | High | $IC_{50}$ = 93.5 µg/mL (API) and 9.6 µg/mL |
| | | DC | High | $IC_{50}$ = 17 µg/mL |
| | SIV | Reverse transcriptase | High | $IC_{50}$ = 4 µg/mL |
| | HSV-2 | Plaque | High | $IC_{50}$ = 1 µg/mL (HSV-2) and 30 µg/mL (HSV-1) |
| | CMV | Binding | Moderate | $IC_{50}$ = 50 µg/mL |
| | Chlamydia (CT) | Multiplication | High | $IC_{50}$ = 28 µg/mL; 100% inhibition at 2 mg/mL |
| | Gonococcus (GC) | Multiplication | Moderate | 100% inhibition at 1 mg/mL. No dose-response |

It is believed that this is the first report of suramin displaying antibacterial activity. Suramin showed inhibiting activity against *Chlamydia trachomatis* and *Neisseria gonorrhoeae*, two of the most prevalent sexually transmitted pathogens. This antibacterial activity of suramin could not have been predicted based on its known antiviral or trypanocidal activity.

Example 3

Local Toxicity

Vaginal Cytotoxicity

Vaginal cytotoxicity was determined by 3-[4,5-dimethylthiazol-2-yl]-2,5-diphenyl tetrazolium bromide (MTT) assay and cytokine assays, both as described in Fichorova R. N. et al., J. Infect. Dis. 184(4): 418-28, 2001). The MTT assay assesses the cytotoxicity of various compounds against cell lines by plating the desired cells prior to exposure to the compounds. On the day of treatment, culture medium was carefully aspirated from the wells and replaced with fresh medium containing the test compound at various concentrations. The cells were incubated with the various compounds for 6 hours, washed with fresh medium and MTT was then added and the plates were incubated at 37° C. for a period of time sufficient to allow MTT to form formazan crystals by reacting with metabolically active cells. The formazan crystals were solubilized overnight at 37° C. in a solution containing 10% SDS in 0.01 M HCl. The absorbance of each well was measured in a microplate reader (Dynex) at 540 nm and a reference wavelength of 690 nm.

Interleukin levels were assessed in the supernatant collected after 6 hours of compound-cells incubation using commercial ELISA kits (R&D Diagnostics, Minneapolis, Minn.) according to manufacturer's instructions (also see Fichorova R. N. et al., J. Infect. Dis. 184(4): 418-28, 2001).

Figure 11:
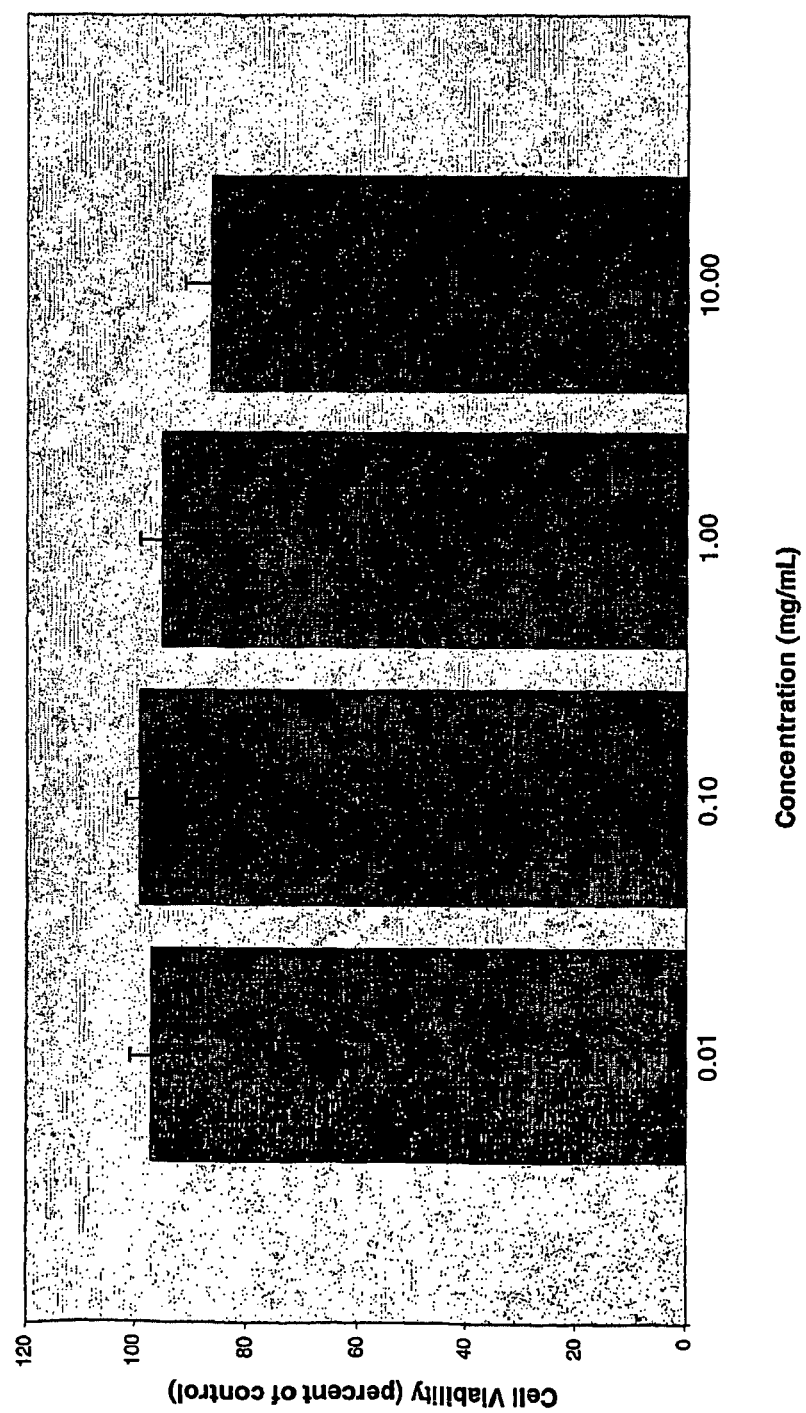
FIG. 11 is a bar graph showing vaginal cell viability as a function of indicated concentrations of suramin as more fully described in Example 3.

Incubated with a human vaginal cell line (VK2) for 30 minutes, 6 hours, and 24 hours at concentrations ranging from 10 mg/mL to 10 µg/mL in a MTT assay, as described above, suramin sodium showed no evidence of cytotoxicity (FIG. 11). This finding was reinforced by the lack of cytotoxic effects described in the antimicrobial assays using different cell lines such as MT-2, HeLa, CaSKi, and others. In a comparative study with dextran sulfate, cellulose sulfate, and N-9, suramin sodium was the least cytotoxic of them all. Another element that enables the use of suramin formulations as a vaginal method to prevent sexual transmission of HIV is the demonstration of its lack of deleterious effects on the vaginal environment. Suramin was proved to be safe to the vaginal epithelial lining and the lactobacilli (beneficial bacterial that keep pathogenic bacterial growth in check). Furthermore, suramin did not induce a proinflammatory reaction, and reduced the inflammation caused by surfactants. Given that surfactants like nonoxynol-9 have failed in clinical trials, not because of their poor virucidal activity but, because of the inflammation they caused (Van Damme L. et al., Lancet., 360(9338): 971-7, 2002; Fichorova R. N. et al., J. Infect. Dis. 184(4): 418-28, 2001), a combination with suramin, which displayed anti-inflammatory activity, appears to be ideal.

Proinflammatory Cytokines

Figure 12:
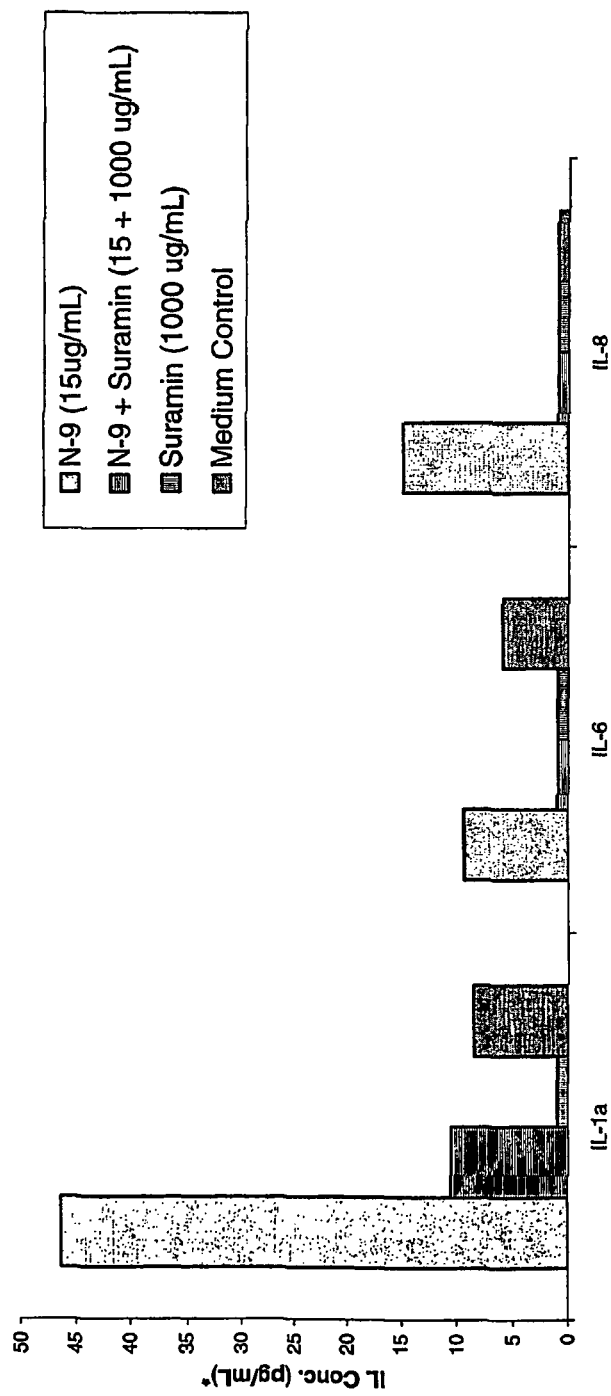
FIG. 12 is a bar graph showing the concentration of indicated interleukins from human vaginal cell supernatants as a function of concentrations of suramin and nonoxynol 9 (N-9). Human vaginal (VK-2) cells were cultured for 6 hours in the presence or absence of the indicated compositions as more fully described in Example 3. Interleukin (EL) concentrations were determined in the cell supernatants. Results are expressed in EL concentration (pg/mL) normalized by percentage of cell viability.

Suramin sodium did not induce the release of IL-1β by cultured vaginal cells in an ELISA assay. This was in sharp contrast with N-9's and other surfactants' effects. Similar results were obtained with IL-1a IL-6, IL-8, and IL-18 (data not shown) as partially seen in FIG. 12. There was no stimulation of proinflammatory cytokines. Furthermore, suramin sodium decreased N-9-induced release of IL-1 and IL-8 by vaginal cells, therefore exerting anti-inflammatory activity (FIG. 12). This activity should be of relevance to decrease the number of leukocytes that serve as targets of HIV infection.

Lactobacilli Growth

Figure 13:
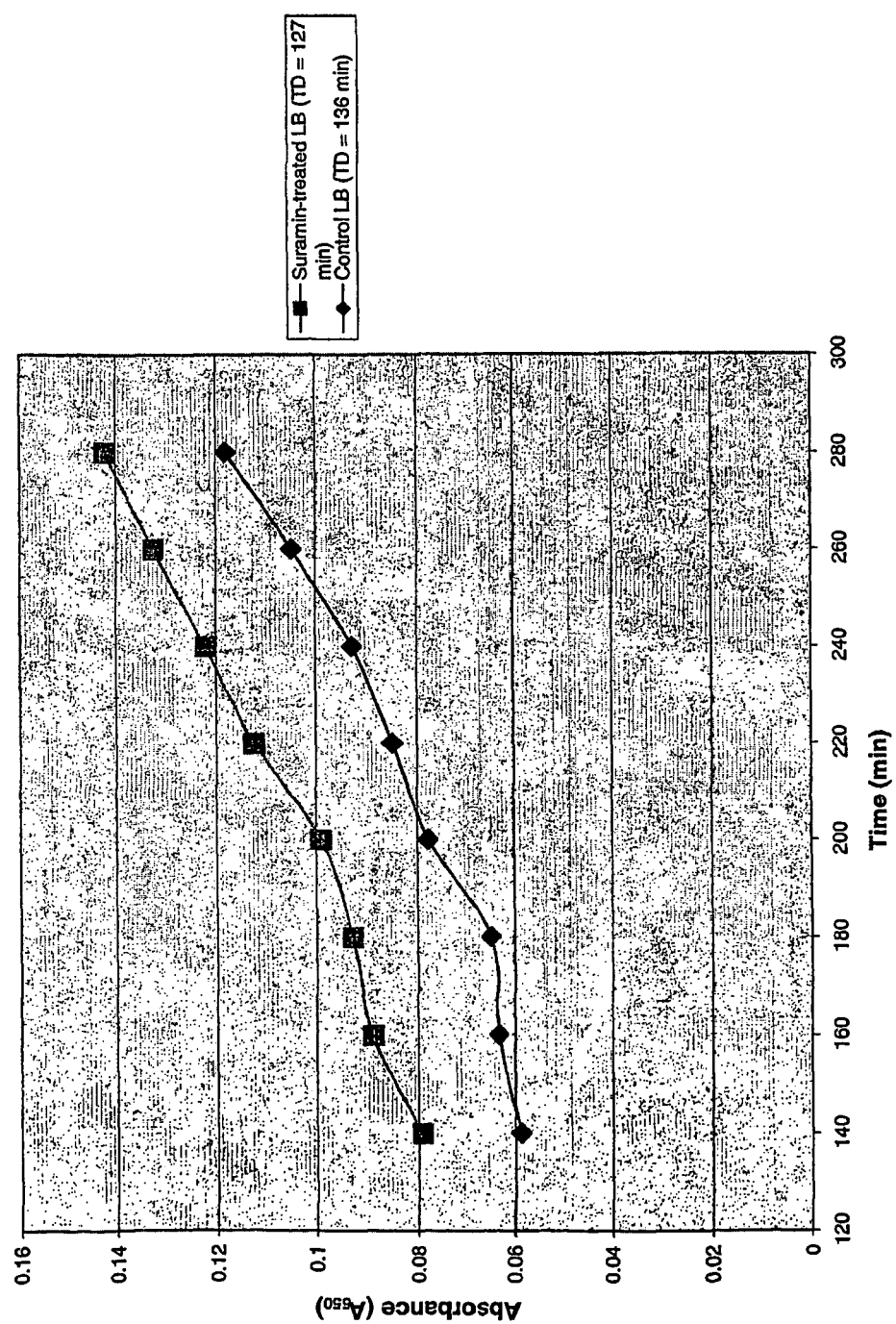
FIG. 13 is a graph showing the effect of suramin on growth of *Lactobacillus* as more fully described in Example 3. $r^2$ (coefficient of correlation)=0.996. TD, doubling time.

Suramin sodium evaluated at 5 mg/mL (highest concentration tested) had no inhibitory effect on the growth of *Lactobacillus gasseri* (growth was 107% of control's) (FIG. 13).

A summary of the local toxicity activity is presented in the following Table 10:

TABLE 10

Local Toxicity Activity of Suramin Compositions.

| Type of Activity | Inhibition/ Inactivation | Assays | Potency | Comments |
| --- | --- | --- | --- | --- |
| Local Toxicity (in vitro) | Lactobacilli | Doubling time | None | Max. concentration tested = 5 mg/mL |
| | Vaginal Cell | MTT | None | Max. concentration |

TABLE 10-continued

Local Toxicity Activity of Suramin Compositions.

| Type of Activity | Inhibition/ Inactivation | Assays | Potency | Comments |
| --- | --- | --- | --- | --- |
| | Cytotoxicity | | | tested = 10 mg/mL (various cell types) |
| | Proinflammatory Cytokines | ELISA | None | IL-1β, IL-1∀, IL-8, IL-6, IL-18 (decreases N-9 induced cytokine release) |

Example 4

Pharmacokinetics

Given that suramin had been abandoned as a therapeutic agent due in great part to its systemic adverse-effects, it was critical to the feasibility of its use as a vaginal preventative anti-STD pathogen method (this application) to demonstrate low bioavailability from the vaginal compartment.

Female rats (n=6) were administered with 30 mg of compound per kg in a single I.V. dose in saline or intravaginally, BID, for 5 days, formulated in KY jelly. The selected single dose represented 10 times the estimated human dose (250 mg). No clinical signs were observed during the conduct of this study. Following intravenous administration, relatively high concentrations of suramin sodium (mean value=563 µg/mL) were measured in plasma at 1 hour (first time-point) following the onset of dosing. Suramin sodium appeared to be eliminated slowly following this route of administration as suggested by the long mean half-life value (68.5 hr) and the small mean clearance value (1.75 mL/hr). The mean volume of distribution was calculated at 147 mL/kg.

Following intravaginal administration, relatively low concentrations of the compound (mean value=17.7 µg/mL) were measured in plasma at 3.5 hours following the last dose. Suramin sodium appeared to be eliminated slowly following intravaginal administration as suggested by the long mean half-life value (132 hr, ~5.5 days) and the small mean clearance value (0.006 mL/hr).

The bioavailability calculated from the total dose (90 mg) administered intravaginally was negligible at 0.8%. No histological lesions were observed in selected tissues (vagina, lungs, liver and kidneys) of female rats receiving the intravenous solution of the compound.

Due to very poor systemic absorption after oral administration, suramin has been administered intravenously in the past. Furthermore, due to its high protein-binding affinity, it was administered in large (gram) quantities. Large doses of suramin I.V. showed side-effects which reduced its therapeutic index as a systemic anti-HIV drug. Thus, clinical trials were not expanded, and the compound was not pursued further. However, in the proposed use as a mucosal (vaginal) microbicide and contraceptive, poor systemic absorption is an advantage, since it limits its action to the site of administration and prevents the development of systemic side-effects. As described above, pharmacokinetics studies performed demonstrated negligible (<1%) bioavailability after vaginal administration.

A summary of the pharmacokinetics analysis is provided in Table 11.

TABLE 11

Summary of Pharmacokinetics Analysis, showing the mean and individual pharmacokinetic parameters of suramin in plasma of female rats following intravenous infusion and intravaginal administration at a dose of 30 mg/kg

| Group | Kel | Cmax (µg/mL) | AUC(tf) (µg-hr/mL) | AUC(I) (µg-hr/mL) | t½ (hr) | Vdss (mL/kg) | CL (mL/hr) |
|---|---|---|---|---|---|---|---|
| IV | 0.0102 | 563 | 13857 | 17289 | 68.6 | 147 | 1.75 |
| Ivag | 0.005 | 17.7 | 1174 | 2275 | 2275 | 132 | 0.006 |

IV: A single intravenous dose of 30 mg/kg
IVag: Intravaginal doses of 30 mg/kg BID for 5 days
AUC(I): The area under the plasma concentration vs time curve from time zero to infinity
AUC(tf): The area under the plasma concentration vs time curve from time zero to 144 hr post dose
CL: Plasma clearance
Cmax: The highest observable concentration
Kel: Elimination constent
Tmax: Time to Cmax
t½ Terminal phase half-life
Vdss: Apparent volume of distribution at steady state All publications mentioned in this specification are herein incorporated by reference, to the same extent as if each individual publication was specifically and individually indicated to be incorporated by reference.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

What is claimed is:

1. A method for simultaneously inhibiting sexually transmitted infections and inhibiting sperm-egg fertilization comprising administering to a female intravaginally, to the cervix or to the uterus a composition comprising a sperm-function inhibitor and suramin in an amount effective to inhibit sexually transmitted infections and sperm-egg fertilization, wherein said sexually transmitted infections are caused by a microorganism selected from the group consisting of *Neisseria gonorrhoeae, Treponema pallidum, Haemophilus ducreyi, Calymmatobacterium granulomatis, Mycoplasma gentitalium*, and *Ureaplasma urealyticum*.

2. The method of claim 1, wherein said microorganism is *Neisseria gonorrhoeae*.

3. The method of claim 1, wherein the sperm-function inhibitor is selected from the group consisting of a nonionic surfactant, a cationic surfactant, an anionic surfactant, a zwitterionic surfactant, a spermicide, a sperm inactivator, an antimicrobial peptide, and an acid buffering composition.

4. The method of claim 1, wherein the sperm-function inhibitor is sorbitan monolaurate.

5. The method of claim 3, wherein the sperm-function inhibitor is a sperm-inactivator selected from the group consisting of polystyrene sulfonate, mandelic acid condensation polymers, and cyclodextrins.

6. The method of claim 3, wherein the sperm-function inhibitor is an antimicrobial peptide selected from the group consisting of gramicidin, magainin, indolicidin, and melittin.

7. The method of claim 3, wherein the sperm-function inhibitor is an acid buffering composition selected from the group consisting of polycarboxylic acid and lactic acid.

8. The method of claim 1, wherein the suramin comprises from about 0.01% to about 30% by weight of the composition.

9. The method of claim 8, wherein the suramin comprises from about 0.05% to about 10% by weight of the composition.

* * * * *